(12) United States Patent
Loddenkemper et al.

(10) Patent No.: US 12,711,615 B2
(45) Date of Patent: Aug. 18, 2026

(54) VIDEO-BASED AUTOMATED DETECTION OF GENERALIZED TONIC-CLONIC SEIZURES USING DEEP LEARNING

(71) Applicant: The Children's Medical Center Corporation, Boston, MA (US)

(72) Inventors: Tobias Loddenkemper, Boston, MA (US); Christian Meisel, Boston, MA (US)

(73) Assignee: The Children's Medical Center Corporation, Boston, MA (US)

( * ) Notice: Subject to any disclaimer, the term of this patent is extended or adjusted under 35 U.S.C. 154(b) by 288 days.

(21) Appl. No.: 18/230,042

(22) Filed: Aug. 3, 2023

(65) Prior Publication Data

US 2023/0386025 A1 Nov. 30, 2023

Related U.S. Application Data

(63) Continuation of application No. PCT/US2022/014212, filed on Jan. 28, 2022.
(Continued)

(51) Int. Cl.
*G06T 7/00* (2017.01)
*A61B 5/00* (2006.01)

(52) U.S. Cl.
CPC ............ *G06T 7/0012* (2013.01); *A61B 5/746* (2013.01); *G06T 2207/10016* (2013.01);
(Continued)

(58) Field of Classification Search
CPC ...... G06V 10/82; G06V 10/764; G06V 40/20; G06V 20/41; G06V 20/44; G06V 20/46;
(Continued)

(56) References Cited

U.S. PATENT DOCUMENTS 10,098,580 B2 * 10/2018 Ng ......................... H04N 23/60
11,564,617 B2 * 1/2023 Nogueira .............. G16H 50/30
(Continued)

OTHER PUBLICATIONS

International Search Report and Written Opinion mailed May 11, 2022 in corresponding International PCT Patent Application No. PCT/US2022/014212 (6 pages).
(Continued)

*Primary Examiner* — Tsung Yin Tsai
(74) *Attorney, Agent, or Firm* — Greenberg Traurig, LLP; Melissa Hunter-Ensor; Kristopher Reichlen

(57) ABSTRACT

Systems and methods of the present disclosure determine whether the patient experiences a grand tonic clonic seizures using video recordings or sensor data or both. The systems and methods receive data from a device that continuously records video and/or sensor data, continuously analyzes the data with a processing unit utilizing machine learning to classify segments of the data as seizure or no seizure, and to classify seizure types. An alarm is produced using an output unit when an epileptic data segment is detected. The processing unit thus provides continuous and in real-time monitoring of an epilepsy patient in the home or hospital setting, e.g. while the patient is sleeping in bed. In case a seizure is detected, an alarm may inform caregivers or clinicians to help them intervene and limit the complications of this seizure for the patient.

20 Claims, 15 Drawing Sheets

Related U.S. Application Data

(60) Provisional application No. 63/276,512, filed on Nov. 5, 2021, provisional application No. 63/146,431, filed on Feb. 5, 2021.

(52) U.S. Cl.
CPC ............... *G06T 2207/20081* (2013.01); *G06T 2207/20084* (2013.01); *G06T 2207/30004* (2013.01)

(58) Field of Classification Search
CPC ........ G06V 20/52; G06V 20/40; G06V 10/40; G06V 10/454; G06V 10/88; G06V 20/49; G06V 10/22; G06V 10/25; G06V 10/7784; G06V 10/811; G06V 10/98; G06V 20/20; G06V 40/10; A61B 5/4094; A61B 5/7264; A61B 5/1128; A61B 5/746; A61B 5/7405; A61B 5/742; A61B 5/0022; A61B 5/0077; A61B 5/01; A61B 5/02055; A61B 5/1113; A61B 5/681; A61B 5/7267; A61B 5/7275; A61B 2562/0219; A61B 3/113; A61B 5/0024; A61B 5/021; A61B 5/02416; A61B 5/02438; A61B 5/0261; A61B 5/0533; A61B 5/0816; A61B 5/11; A61B 5/1118; A61B 5/14542; A61B 5/6814; A61B 5/6816; A61B 5/6823; A61B 5/6898; A61B 5/7203; A61B 5/7207; A61B 5/7278; A61B 5/747; A61B 7/04; A61B 5/318; A61B 5/389; A61B 5/4082; A61B 5/4842; G06N 20/00; G06N 3/08; G06N 3/0464; G06N 3/09; G06N 3/045; G06N 20/20; G06N 3/0442; G06N 3/0499; G06N 7/01; G06N 3/04; G06N 3/044; G06N 3/096; G06N 5/01; G16H 50/20; G16H 20/10; G16H 40/63; G16H 40/67; G16H 50/70; G16H 20/30; G16H 30/40; G16H 50/30; G16H 20/40; G16H 80/00; G16H 10/60; G16H 20/00; G16H 30/20; G06F 18/214; G06F 18/24; G06F 18/256; G06F 16/2465; G06F 16/35; G06F 21/552; G06F 2221/034; G06F 16/71; G06F 18/2178; G06F 18/2411; G06F 18/2413; G06F 18/24323; G06F 18/2451; G06F 18/25; G06F 18/285; G06T 2207/10016; G06T 2207/20081; G06T 2207/20084; G06T 2207/30004; G06T 7/0012; G08B 13/19615; G08B 13/19671; G08B 13/19682; G08B 7/06; G08B 31/00; G06Q 10/0635; G09B 19/00; G09B 19/0092; G09B 23/28; G10L 15/063; G10L 15/24; G10L 15/26; H04N 21/2187; H04N 21/251; H04N 21/25891; H04N 21/26291
See application file for complete search history.

(56) References Cited

U.S. PATENT DOCUMENTS

| | | | | |
|---|---|---|---|---|
| 12,266,185 | B2 * | 4/2025 | Radhakrishnen | G06V 10/82 |
| 2016/0220169 | A1 * | 8/2016 | Girouard | A61B 5/4094 |
| 2017/0035330 | A1 * | 2/2017 | Bunn | A61B 5/1124 |
| 2017/0196497 | A1 | 7/2017 | Ray et al. | |
| 2018/0206776 | A1 * | 7/2018 | Nogueira | G16H 20/00 |
| 2018/0249964 | A1 * | 9/2018 | Qian | A61B 5/0245 |
| 2019/0298248 | A1 * | 10/2019 | Loddenkemper | A61B 5/4094 |
| 2020/0117901 | A1 | 4/2020 | McClernon et al. | |
| 2020/0155114 | A1 * | 5/2020 | Park | A61B 8/463 |
| 2021/0100492 | A1 * | 4/2021 | Knight | G06V 10/82 |
| 2023/0071470 | A1 * | 3/2023 | Radhakrishnen | G06V 10/774 |
| 2023/0141496 | A1 * | 5/2023 | Loddenkemper | G16H 40/63 600/300 |

OTHER PUBLICATIONS

Yang et al., "Video-Based Detection of Generalized Tonic-Clonic Seizures Using Deep Learning (v1)," IEEE Journal of Biomedical and Health Informatics, Jan. 6, 2021, vol. 25, No. 8, pp. 1-15.
Extended European Search Report dated Nov. 22, 2024, in corresponding European Patent Application No. 22750208.5 (8 pages).
Office Action dated Dec. 12, 2025, in corresponding European Patent Application No. 22750208.5 (6 pages).

* cited by examiner

Matching ictal and interictal video sequences

Leave-one-out cross validation

Sensitivity [%]

Specificity [%]

Seizures

Total Time [minutes]
Patient

Matching ictal and interictal video sequences

Leave-one-out cross validation

VIDEO-BASED AUTOMATED DETECTION OF GENERALIZED TONIC-CLONIC SEIZURES USING DEEP LEARNING

CROSS REFERENCE TO RELATED APPLICATIONS

This application is a continuation under 35 U.S.C. § 111(a) of PCT International Patent Application No. PCT/US2022/014212, filed Jan. 28, 2022, designating the United States and published in English, which claims priority to and the benefit of U.S. Provisional Application No. 63/146,431, filed Feb. 5, 2021, and U.S. Provisional Application No. 63/276,512, filed Nov. 5, 2021, the entire contents of each of which are incorporated by reference herein.

BACKGROUND

The timely detection of epileptic seizures is important to prevent potential complications from seizures such a secondary injuries, falls, to alert caregivers and provide timely treatment e.g. to stop a seizure. In patients with generalized tonic-clonic seizures (GTCS), timely detection of seizures may be particularly crucial in order to prevent the occurrence of sudden death in epilepsy (SUDEP). Video-EEG seizure monitoring is considered the gold-standard in detecting epileptic seizures. It is routinely performed in specialized epilepsy monitoring units (EMUs) due to its essential role for the diagnosis and treatment of epilepsy. Despite its value, however, in-patient video monitoring and its evaluation is time- and labor-consuming in the hospitals where it is available. Furthermore, in the majority of hospitals and in the home setting, video monitoring is limited due to resource constraints, although video surveillance techniques are becoming more affordable. Most patients monitor seizures at home with monitoring devices either designed for baby monitoring, or with one device by a company (Sami monitor), that does not specifically detect seizure movements on video. Automated video-based seizure detection methods that allow the detection of seizures, in particular GTCS, would allow a better monitoring and optimizing of treatments, the prevention of secondary complications, such as lowering the risk of SUDEP, in more broad hospital and home settings. It would also allow to reduce the time and labor involved in screening and evaluating long-term video-EEG data in specialized EMU settings. The current invention discloses a self-contained, automated video detection system to detect GTCS and alarm caregivers of a seizure occurring in real-time.

Definitions

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

As used herein, the term "data stream" refers to a periodic or continuous transmission of data from one system, device, or component to another via any suitable wired or wireless data communication devices and techniques.

As used herein, the term "tonic clonic seizure" refers to a type of seizure, also known as a grand mal seizure, characterized by a tonic phase where the body becomes rigid, followed by a clonic phased where the body undergoes uncontrolled jerking. Seizures may have a focal onset, with secondary generalization and evolution into generalized tonic clonic seizure.

As used herein, the term "ictal" refers to the period a physiologic state or event such as a seizure, and may be used to further indicate the period of a, e.g., stroke, headache, inflammation, flare-up, mental health episode, or in general any relapsing-remitting diseases.

As used herein, the term "preictal" refers to the time period preceding an ictal event of variable duration.

As used herein, the term "interictal" refers to the period between ictal events.

As used herein, the term "postictal" refers to the period refers to the state shortly after an ictal event.

As used herein, the term "periictal" refers to the period encompassing preictal, ictal and postictal periods.

As used herein, the term "frame" refers to a single one in a series of pictures forming a video.

As used herein, the term "electrodermal activity" refers to a measure of neurally mediated effects on sweat gland permeability, observed as changes in the resistance of the skin to a small electrical current, or as differences in the electrical potential between different parts of the skin.

As used herein, the term "integration window" refers to a time period including data on which an operation is to be performed.

As used herein, the term "ground-truth" refers to one or more sets of object, provable data.

As used herein, the term "multi-modal" refers to the statistical distribution of values with multiple peaks.

As used herein, the term "electroencephalography (EEG)" refers to the measurement of electrical activity in different parts of the brain.

As used herein, the term "electrocorticography (ECoG)" refers to e direct recording of electrical potentials associated with brain activity from the cerebral cortex.

As used herein, the term "electrocardiography (ECG)" refers to the measurement of electrical activity in the heart using electrodes placed on the skin of the limbs and chest.

As used herein, the term "biosensor" refers to a device configured to and/or capable of producing data streams of clinical, biological or physiological parameters by sensing such parameters from a patient.

As used herein, the term "train" or "training" refers to the process of updating algorithm weight values in a machine learning model according to error between predict results and actual results.

As used herein, the term "test" or "testing" refers to the process of determining performance metrics of a machine learning model based on differences between predict results and actual results.

As used herein, the term "sensitivity" refers to the true positive seizure prediction rate.

As used herein, the term "time in warning" or "TiW" refers to the fraction of time spent in warning.

As used herein, the term "improvement over chance" or "IOC" refers to the difference between sensitivity and time in warning.

As used herein, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc. It is understood that at least one aspect or functionality of various embodiments described herein can be performed in real-time or dynamically, or both.

As used herein, the terms "computer engine" and "engine" identify at least one software component and/or a combination of at least one software component and at least one hardware component which are designed, programmed or otherwise configured to manage or control other software and hardware components (such as the libraries, software development kits (SDKs), objects, etc.).

As used herein, term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Cloud servers are examples.

As used herein, the term "mobile electronic device," or the like, may refer to any portable electronic device that may or may not be enabled with location tracking functionality (e.g., MAC address, Internet Protocol (IP) address, or the like). For example, a mobile electronic device can include, but is not limited to, a mobile phone, Personal Digital Assistant (PDA), Blackberry™, Pager, Smartphone, or any other reasonable mobile electronic device.

As used herein, terms "proximity detection," "locating," "location data," "location information," and "location tracking" refer to any form of location tracking technology or locating method that can be used to provide a location of, for example, a particular computing device, system or platform of the present disclosure and any associated computing devices, based at least in part on one or more of the following techniques and devices, without limitation: accelerometer(s), gyroscope(s), Global Positioning Systems (GPS); GPS accessed using Bluetooth™; GPS accessed using any reasonable form of wireless and non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, Cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed; this is in no way meant to be a limitation.

As used herein, terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user).

As used herein, the term "user" shall have a meaning of at least one user. In some embodiments, the terms "user", "subscriber" "consumer" or "customer" should be understood to refer to a user of an application or applications as described herein and/or a consumer of data supplied by a data provider. By way of example, and not limitation, the terms "user" or "subscriber" can refer to a person who receives data provided by the data or service provider over the Internet in a browser session, or can refer to an automated software application which receives the data and stores or processes the data.

As used herein, the terms "and" and "or" may be used interchangeably to refer to a set of items in both the conjunctive and disjunctive in order to encompass the full description of combinations and alternatives of the items. By way of example, a set of items may be listed with the disjunctive "or", or with the conjunction "and." In either case, the set is to be interpreted as meaning each of the items singularly as alternatives, as well as any combination of the listed items.

SUMMARY OF THE DISCLOSURE

Embodiments of the present disclosure provide one or more methods for detecting seizure occurrences in video data. The one or more methods include receiving, by at least one processor, real-time video data including a continuous video feed of a patient location;

extracting, by the at least one processor, an epoch of video data including a video segment from the continuous video feed from a patient monitoring period preceding a current time;

generating, by the at least one processor, time-series data representative of the epoch of video data;

utilizing, by the at least one processor, seizure recognition machine learning model to determine a seizure classification of the video segment including either a seizure video segment classification or no-seizure video segment classification based on the time-series data and learned model parameters; and causing to produce, by the at least one processor, a seizure indication at a computing device associated with a caregiver for each video segment identified as a seizure video segment to alert the caregiver of a seizure.

In some embodiments, the method further includes encoding, by the at least one processor, the epoch of video data into the time-series data using a pre-trained encoding model.

In some embodiments, the method further includes where the pre-trained encoding model includes MobileNet.

In some embodiments, the method further includes downsampling, by the at least one processor, the video segment by downsample one of: i) frame rate, ii) color data, iii) resolution, or iv) combinations thereof.

In some embodiments, the method further includes where the seizure recognition machine learning model includes a recurrent neural network.

In some embodiments, the method further includes where the seizure recognition machine learning model includes a long short-term memory network.

In some embodiments, the method further includes determining, by the at least one processor, a seizure probability value using the seizure recognition machine learning model based on the time-series data; and determining, by the at least one processor, the seizure classification of the video segment based on a comparison of the seizure probability value to a classification threshold.

In some embodiments, the method further includes where the seizure classification includes the no seizure video segment classification where the seizure probably value is less than the classification threshold.

In some embodiments, the method further includes where the patient monitoring period includes 5 seconds associated with the epoch of video data including 5 seconds of video data.

In some embodiments, the method further includes utilizing, by the at least one processor, the seizure recognition machine learning model for each subsequent epoch of video data received in the continuous video feed.

Embodiments of the present disclosure provide one or more methods for detecting seizure occurrences in sensor data. The one or more methods include receiving, by at least one processor, real-time video data including a continuous video feed of a patient location; extracting, by the at least one processor, an epoch of video data including a video segment from the continuous video feed from a patient monitoring period preceding a current time; receiving, by at least one processor, real-time biometric sensor data including a continuous feed of biometric measurements; extracting, by the at least one processor, an epoch of biometric sensor data including a biometric measurement segment from the continuous feed of biometric measurements from the patient monitoring period preceding the current time; generating, by the at least one processor, time-series data representative of the epoch of video data and the epoch of biometric sensor data; utilizing, by the at least one processor, seizure recognition machine learning model to determine a seizure classification for the patient monitoring period based on the time-series data and learned model parameters; and causing to produce, by the at least one processor, a seizure indication at a computing device associated with a caregiver for the patient monitoring period that indicates the seizure classification to alert the caregiver.

In some embodiments, the method further includes encoding, by the at least one processor, the epoch of video data into the time-series data using a pre-trained encoding model.

In some embodiments, the method further includes where the biometric sensor includes at least one of: a surface electromyography (sEMG) sensor, an electrodermal activity (EDA) sensor, an electrocardiogram (EKG) sensor, a photoplethysmography (PPG) sensor, an accelerometer, a mattress sensor, a cerebral oxygen saturation sensor, a near-infrared spectroscopy (NIRS) sensor, an implanted advisory system, a skin temperature sensor, a respiratory monitor, a magnetometer, and a gyroscope.

In some embodiments, the method further includes downsampling, by the at least one processor, the video segment by downsample one of: i) frame rate, ii) color data, iii) resolution, or iv) combinations thereof.

In some embodiments, the method further includes where the seizure recognition machine learning model includes a recurrent neural network.

In some embodiments, the method further includes where the seizure recognition machine learning model includes a long short-term memory network.

In some embodiments, the method further includes determining, by the at least one processor, a seizure probability value using the seizure recognition machine learning model based on the time-series data; and determining, by the at least one processor, the seizure classification based on a comparison of the seizure probability value to a classification threshold.

In some embodiments, the method further includes where the seizure classification includes a no seizure classification where the seizure probability value is less than the classification threshold.

In some embodiments, the method further includes where the patient monitoring period includes 5 seconds associated with the epoch of video data and the epoch of biometric sensor data.

In some embodiments, the method further includes utilizing, by the at least one processor, the seizure recognition machine learning model for each subsequent epoch of video data received in the continuous video feed.

Embodiments of the present disclosure provide one or more systems configured to detect seizure occurrences in video data. The one or more systems include at least one processor configured to receive instructions stored in a non-transitory memory that cause the at least one processor to perform steps to: receive real-time video data including a continuous video feed of a patient location; extract an epoch of video data including a video segment from the continuous video feed from a patient monitoring period preceding a current time; generate time-series data representative of the epoch of video data; utilize seizure recognition machine learning model to determine a seizure classification of the video segment including either a seizure video segment classification or no-seizure video segment classification based on the time-series data and learned model parameters; and cause to produce a seizure indication at a computing device associated with a caregiver for each video segment identified as a seizure video segment to alert the caregiver of a seizure.

In some embodiments, the system is further configured where the at least one processor is further configured to receive instructions causing the at least one processor to perform steps to encode the epoch of video data into the time-series data using a pre-trained encoding model.

In some embodiments, the system is further configured where the pre-trained encoding model includes MobileNet.

In some embodiments, the system is further configured to receive instructions causing the at least one processor to perform steps to downsample the video segment by downsample one of: i) frame rate, ii) color data, iii) resolution, or iv) combinations thereof.

In some embodiments, the system is further configured where the seizure recognition machine learning model includes a recurrent neural network.

In some embodiments, the system is further configured where the seizure recognition machine learning model includes a long short-term memory network.

In some embodiments, the system is further configured to receive instructions causing the at least one processor to perform steps to: determine a seizure probability value using the seizure recognition machine learning model based on the time-series data; and determine the seizure classification of the video segment based on a comparison of the seizure probability value to a classification threshold.

In some embodiments, the system is further configured where the seizure classification includes the no seizure video segment classification where the seizure probably value is less than the classification threshold.

In some embodiments, the system is further configured where the patient monitoring period includes 5 seconds associated with the epoch of video data including 5 seconds of video data.

In some embodiments, the system is further configured to receive instructions causing the at least one processor to perform steps to utilize the seizure recognition machine learning model for each subsequent epoch of video data received in the continuous video feed.

Embodiments of the present disclosure provide one or more systems configured to detect seizure occurrences in sensor data. The one or more systems include at least one processor configured to receive instructions stored in a non-transitory memory that cause the at least one processor to perform steps to: receive real-time video data including a continuous video feed of a patient location; extract an epoch of video data including a video segment from the continuous video feed from a patient monitoring period preceding a current time; receive real-time biometric sensor data including a continuous feed of biometric measurements; extract an epoch of biometric sensor data including a biometric measurement segment from the continuous feed of biometric measurements from the patient monitoring period preceding the current time; generate time-series data representative of the epoch of video data and the epoch of biometric sensor data; utilize seizure recognition machine learning model to determine a seizure classification for the patient monitoring period based on the time-series data and learned model parameters; and cause to produce a seizure indication at a computing device associated with a caregiver for the patient monitoring period that indicates the seizure classification to alert the caregiver.

In some embodiments, the system is further configured to receive instructions causing the at least one processor to perform steps to encode the epoch of video data into the time-series data using a pre-trained encoding model.

In some embodiments, the system is further configured where the biometric sensor includes at least one of: a surface electromyography (sEMG) sensor, an electrodermal activity (EDA) sensor, an electrocardiogram (EKG) sensor, a photoplethysmography (PPG) sensor, an accelerometer, a mattress sensor, a cerebral oxygen saturation sensor, a near-infrared spectroscopy (NIRS) sensor, an implanted advisory system, a skin temperature sensor, a respiratory monitor, a magnetometer, and a gyroscope.

In some embodiments, the system is further configured to receive instructions causing the at least one processor to perform steps to downsample the video segment by downsample one of: i) frame rate, ii) color data, iii) resolution, or iv) combinations thereof.

In some embodiments, the system is further configured where the seizure recognition machine learning model includes a recurrent neural network.

In some embodiments, the system is further configured where the seizure recognition machine learning model includes a long short-term memory network.

In some embodiments, the system is further configured to receive instructions causing the at least one processor to perform steps to: determine a seizure probability value using the seizure recognition machine learning model based on the time-series data; and determine the seizure classification of the video segment based on a comparison of the seizure probability value to a classification threshold.

In some embodiments, the system is further configured where the seizure classification includes a no seizure classification where the seizure probability value is less than the classification threshold.

In some embodiments, the system is further configured where the patient monitoring period includes a time period of 5 seconds associated with the epoch of video data and the epoch of biometric sensor data.

In some embodiments, the system is further configured where the at least one processor is further configured to receive instructions causing the at least one processor to perform steps to utilize the seizure recognition machine learning model for each subsequent epoch of video data received in the continuous video feed.

BRIEF DESCRIPTION OF THE DRAWINGS

FIG. 4A depicts consecutive ictal video clips of 5 seconds duration (red) were matched with the same number of interictal video clips (green) for each patient, in accordance with one or more embodiments of the present invention. FIG. 4B depicts a leave-one-out cross-validation approach that trained on matched data from all but one patient and evaluated on the full data from the remaining patient was implemented to assess performance, in accordance with one or more embodiments of the present invention.

FIG. 6A depicts predicted seizure likelihood for one seizure, where likelihood is assessed every 5 seconds; if likelihood is smaller than 0.5 no seizure is detected (light gray), otherwise a seizure is detected during this 5-second epoch (dark gray), in accordance with one or more embodiments of the present invention. FIG. 6B depicts the likelihood time course for all seizures, where black vertical lines indicate the first time another person aside from the patient is visible in the video and black round markers indicate the onset of the tonic phase, in accordance with one or more embodiments of the present invention.

DETAILED DESCRIPTION

Figure 1:
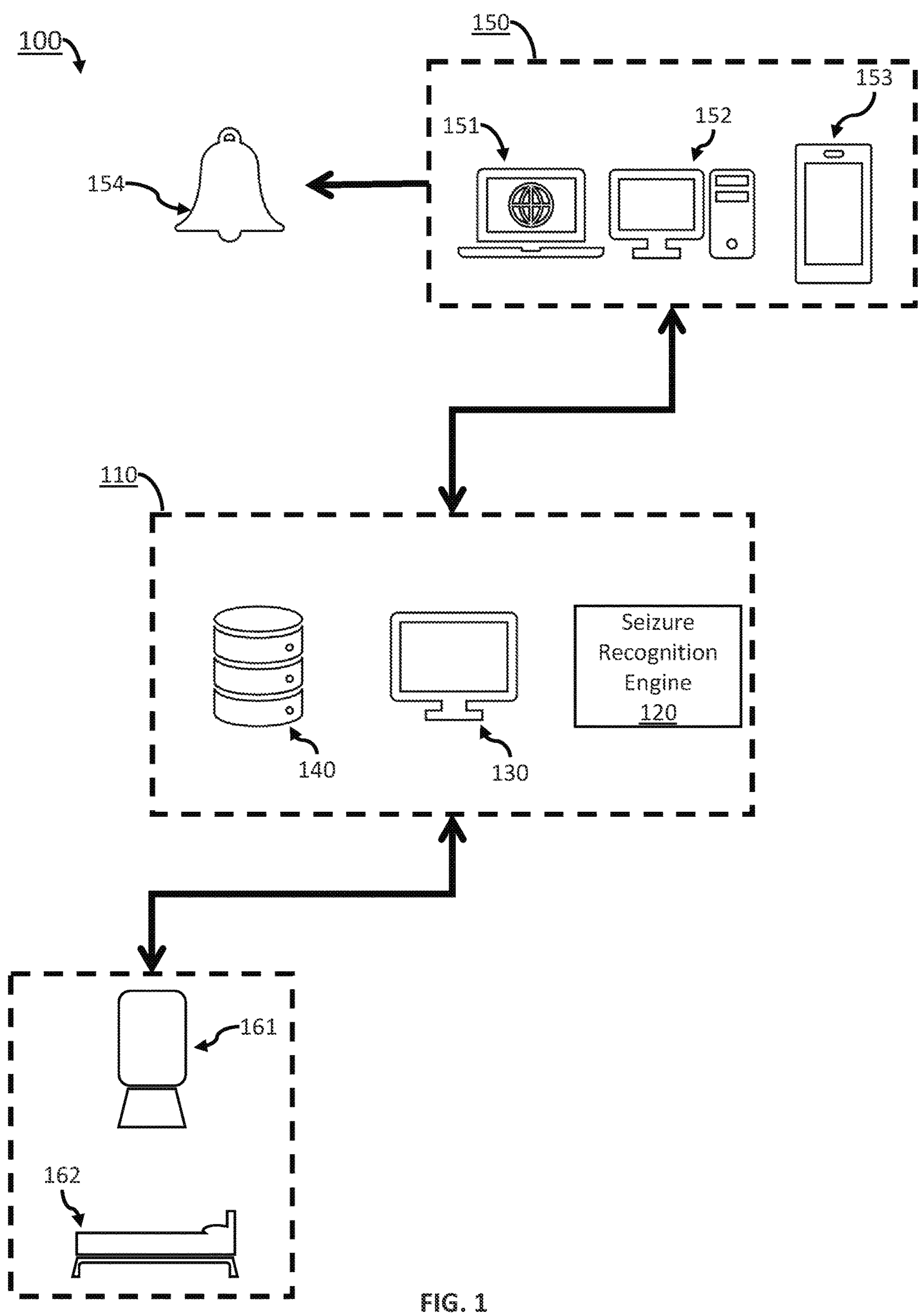
FIG. 1 illustrates an example of a schematic outline of a system for video-based detection of seizures including a video camera unit to record video data of a patient, a data processing unit to determine whether a video shows an epileptic seizure or not, and an alarm unit to provide an alarm once a seizure is detected, in accordance with one or more embodiments of the present invention.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

In order to enable healthcare facilities to continuously and in real-time monitor an epilepsy patient in the home or hospital setting, e.g. while the patient is sleeping in bed, the embodiments of the present invention include systems and methods to automatically determine whether the patient experiences a particular seizure type, such as, e.g., general tonic-clonic seizure (GTCS), using sensor recordings, including, e.g., video sequences, image sequences, sensor signal sequences, among other sequences of sensor readings or any combination thereof. By employing a processing unit equipped with machine learning models trained to detection a patient's physical signs and symptoms of a seizure, embodiments of the present invention can continuously analyze the sensor data with the trained machine learning models and provide an alarm when movements indicative of a current or prospective epileptic episode is detected. Thus, a seizure is automatically detected at the time of an impending seizure, rather than at a time that a caregiver happens to be monitoring the patient and with better accuracy than traditional vital sign monitoring. Thus, the system provides new technical capabilities for around the clock monitoring of epileptic patients with means to start off an alarm to inform caregivers or clinicians to help them intervene and limit the complications of this seizure for the patient. Thus, the typical systems of combinations of in-person and vital measurement seizure detection are improved upon by providing a seizure detection system employing machine learning models that can better provide real-time and continuous automatic detection and notification of a seizure.

In some embodiments, by using a combination of sensors, such as video capture devices and additional biometric sensor devices, enables an improved a seizure monitoring system that requires no intervention by the user (no wires or wearables) to improve upon video-only or sensor-only monitoring approaches, which maximizes nightly adherence and subject comfort. In some embodiments, the fusion of the video and biometric sensor-based signals results in high accuracy and low false rate, reducing caretaker alarm fatigue experienced by current home monitoring systems. In some embodiments, the video and the biometric sensor signals may be combined for use with machine learning-based, video detection algorithm on a commercially available video monitoring platform, biometric sensor-based respiratory rate detection, to deliver a superior video-biometric sensor monitoring system for nighttime seizures in patients' homes.

In some embodiments, optimized machine learning techniques may be employed that are adapted to the hardware specifications of an exemplary multi-sensor monitoring system, including, e.g., video sampling rate, pixel resolution and computational power, among other specifications.

In some embodiments, optimized machine learning techniques may be employed that are optimized for generalized tonic-clonic seizure detection using all collected multi-sensor monitoring system data, including biometric sensor sensing using the best performing overall algorithm to detect seizures of a seizure type from video and biometric sensor modalities with optimal sensitivity, specificity, and low false alarm rate and detection latency.

A seizure may be considered a "symptom . . . of an occasional, an excessive and a disorderly discharge of nerve tissue". The definition of epileptic seizure may include, "a transient occurrence of signs and/or symptoms due to abnormal excessive or synchronous neuronal activity in the brain". Specific seizure types have varying features that may enable detection. In some embodiments, the multi-sensor monitoring system may include one or more sensors for the detection of various types of seizures. Indeed, some seizures are more effectively identified using particular sensors.

Knowing the main semiological components of seizures is a basic initial step in the process of selecting the best seizure detection device for each patient. Each seizure type may include one or more phenomena occurring simultaneously or sequentially. In order to evaluate clinical features, the two main components that can be assessed are movement and physiological signals. The movement refers to specific body parts, as the limbs involved in a GTCS, or head or eye deviation. These could be detected by accelerometry, surface electromyography (sEMG), video monitoring, mattress sensors, electro-oculogram, or seizure alert dogs. The physiological signals include heart rate, respiratory rate, sweating and temperature. These could be detected by electrocardiogram (EKG) or photoplethysmography (PPG), sweating by EDA, temperature by a wristband and changes in respiratory rate with a thoracic band. Seizures may present with body movements and often prominent autonomic changes. Therefore, several sensor types recognize particular seizure types more readily than other seizure types. On the other end of the spectrum, absence are challenging to capture as they consist of a brief decrease in awareness with minimal associated movements, and thus are often only picked up by an observer or by EEG.

In some embodiments, a seizure detection sensor may be able to detect movement in body parts and changes in cognitive function or physiological signals simultaneously. The system could be even more effective if it also interacted with the patient in an active way that could allow testing for awareness or cognitive function. This could be done with a task or gaming device that keeps track of the patient's responsiveness while completing tasks or while playing. If the patient stops playing, or if task performance changes, the device could ask the patient to follow some specific commands, and in turn the system would ideally alert a designated caregiver in the event of impaired performance. This could also be done by robot or external device that wirelessly receives the input of movement and physiological signals from the monitoring device. For example, a wristband analyzes signals in real time, and when parameters are altered, it will interact with the patient to assert for consciousness. This has an advantage compared to a gaming system in that it could interact with the patient when detecting abnormal physiological parameters during the night, whereas the gaming device's functionality is limited to when the patient is awake. An integral system would hypothetically allow detection of all seizure types, including those considered subtle like absence seizures.

Video-Based Seizure Detection

Referring to FIG. 1, an example of a system 100 for video-based seizure detection is illustrated according to embodiments of the present invention.

In some embodiments, a seizure early-warning system 100 may automatically determine whether a patient experiences a GTCS using video recordings. The seizure early-warning system 100 may include a video capture device 161 to continuously record video of a patient location 162, a processing unit 110 to continuously analyze the video data and an alarm unit 150 that provides an alarm 154 when an epileptic video is detected.

In some embodiments, the processing unit 110 may include any type of data processing capacity, such as a hardware logic circuit, for example an application specific integrated circuit (ASIC) and a programmable logic, or such as a computing device, for example, a microcomputer or microcontroller that include a programmable microprocessor. In some embodiments, the processing unit 110 may include data-processing capacity provided by the microprocessor. In some embodiments, the microprocessor may include memory, processing, interface resources, controllers, and counters. In some embodiments, the microprocessor may also include one or more programs stored in memory.

In some embodiments, the processing unit 110 may be a part of a computing device associated with the patient, a caregiver of the patient, a family member of the patient, a healthcare facility or service associated with the patient or where the patient location 162 is located, among other related systems responsible for monitoring health of the patient. In some embodiments, the processing unit 110 may embodied is a user computer, laptop computer, mobile computing device, server or server system, cloud computing system, or other computing system.

In some embodiments, the processing unit 110 may include a database 140 for receiving and storing the received video from the video capture device 161. In some embodiments, the database 140 may be configured to maintain a record of the video for a predetermined period of time, e.g., about a week, a month, 3 months, 6 months, a year, or other suitable length of time. As such, the database 140 may provide video data related to a patient for a period of time to allow a user to review the data, to update or train seizure recognition models of the seizure recognition engine 120, among other uses. As such, the length of time may be any suitable length of time to review the data, update the models, or any other use, subject to the pertinent patient privacy requirements (e.g., HIPPA or other laws and standards).

In some embodiments, the database 140 may be configured to communicate with the seizure recognition engine 120. Accordingly, the seizure recognition engine 120 may ingest data from the database 140 for training and updating seizure recognition models, based on known outcomes for segments of video data. In some embodiments, the video data in the database 140 may also be used to test and evaluation predictions by the seizure recognition engine 120.

In some embodiments, the database 140 may include, e.g., a suitable memory or storage solutions for providing electronic data to the processing unit 110. For example, the database 140 may include, e.g., a centralized or distributed database, cloud storage platform, decentralized system, server or server system, among other storage systems, or the database 140 may include, e.g., a hard drive, solid-state drive, flash drive, or other suitable storage device, or the data storage 112 may include, e.g., a random access memory, cache, buffer, or other suitable memory device, or any other data storage solution and combinations thereof.

In some embodiments, the database 140 may receive and record the continuous stream of video data among other patient data, including electronic medical record data, clinical data, radiological and other imagery and test results, medication and medication dosages, and any other health-related data, such as any data from an electronic medical health record or other health record. The video data may be accessible by, e.g., seizure recognition engine 120, a user terminal 130 and the alarm unit 150. However, in some embodiments, the video data may be provided directly to the seizure recognition engine 120 and the alarm unit 150 before or instead of being stored in the database 140.

In some embodiments, during patient monitoring, the seizure recognition engine 120 may receive video data as a direct feed from the video capture device 161, or indirectly via the database 140, so long as the video data is provided to the seizure recognition engine 120 quickly enough to identify any seizure signs and symptoms and communicate the determination to the alarm unit 150 for alerting a caregiver in time to mitigate hazards associated with a seizure.

In some embodiments, video is recorded in real-time with a video-capture device 161 and sent to the data processing unit 110. In the processing unit 110, the video data is continuously evaluated and automatically classified as either "seizure" or "no seizure" using the seizure recognition engine 120.

In some embodiments, the seizure recognition engine 120 includes a combination of hardware and/or software for inferring a seizure occurrence in real-time based on the video data, or a subset of the video data pertaining to a selected segment of time preceding a current time. In some embodiments, the seizure recognition engine 120 may determine the presence of a seizure occurrence continuously (e.g., using a continuous feed of video data continuously processed with models, e.g., using a rolling time window of video data) or periodically, e.g., once every detection period using a monitoring period of video data. In some embodiments, the detection period may be, e.g., every second, every ten seconds, every fifteen seconds, every twenty seconds, every thirty seconds, every minute, or other suitable period to detect a seizure occurrence in time to notify a caregiver to mitigate hazards. Thus, for each detection period, the seizure recognition engine 120 may develop a seizure occurrence determination for that detection period based on video data of a monitoring period and other health-related data. In some embodiments, the monitoring period may include video data from a suitable period of time for identifying a seizure occurrence, such as, a time window of about, e.g., five second epochs, 10 second epochs, 15 second epochs, 20 second epochs, 30 second epochs, or other time window duration.

In some embodiments, the seizure recognition engine 120 may process each epoch of video data to determine whether each epoch includes video of a seizure occurrence. In some embodiments, the seizure recognition engine 120 may employ machine learning models and techniques trained to detect seizure occurrences based on epochs of the video data. Thus, in some embodiments, the seizure recognition engine 120 may include a machine learning model for differentiating between video of patient activity that indicates "seizure" and activity that indicates "no seizure." To do so, in some embodiments, the seizure recognition engine 120 may include artificial intelligence (AI) or machine learning techniques for generating a binary classification of an epoch of video data at each detection period based on the epoch of video data and, e.g., physiological parameters and physiological data from, e.g., electronic medical health records. In some embodiments, the machine learning models and techniques of the seizure recognition engine 120 may include techniques chosen from, but not limited to, classifiers for use with video data such as, e.g., decision trees, boosting, support-vector machines, neural networks, nearest neighbor algorithms, Naive Bayes, bagging, random forests, and the like. In some embodiments and, optionally, in combination of any embodiment described above or below, an exemplary neutral network technique may be one of, without limitation, feedforward neural network, radial basis function network, recurrent neural network, convolutional network (e.g., U-net), long short-term memory network or other suitable network. In some embodiments and, optionally, in combination of any embodiment described above or below, an exemplary implementation of Neural Network may be executed as follows:

i) define Neural Network architecture/model,
ii) transfer the input data to the exemplary neural network model,
iii) train the exemplary model incrementally,
iv) determine the accuracy for a specific number of timesteps,
v) apply the exemplary trained model to process the newly-received input data, and
vi) optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values, functions and aggregation functions. For example, an activation function of a node may be a step function, sine function, continuous or piecewise linear function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

As used herein, the terms "engine", such as the seizure recognition engine 120, identifies at least one software component or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, programs, applications, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, the classification from the seizure recognition engine 120 can include a binary classification (e.g., "seizure" or "no seizure"). The binary classification can include a probability that at a given detection period the epoch of video data shows patient activity associated with a seizure occurrence. For example, the classification may include a numerical value on a scale from 0 to 1, where 0 indicates a zero percent probability of a seizure occurrence in the epoch of video data, and where 1 indicates a one hundred percent probability of a seizure occurrence in the epoch of video data. In practice, any given prediction period is unlikely to be a or a 1, but likely may be classified somewhere in between. Thus, in some embodiments, the seizure recognition engine 120 may determine a classification for an epoch of video data based on, e.g., a classification threshold. For example, where the probability rises above a classification threshold of, e.g., 0.5, 0.52, 0.54, 0.56, 0.58, 0.6, the seizure recognition engine 120 may determine that the epoch of video data includes patient activity including a seizure occurrence. In some embodiments, the classification may also include additional seizure characteristics, such as, e.g., a seizure type to enable distinguishing different seizure subtypes.

In some embodiments, once a seizure is detected (i.e. data is classified as “seizure”), the connected alarm unit 150 triggers an alarm 154 via a notification device, such as, e.g., a user computing device 151 associated with one or more caregivers of the patient, a facility computing system 152 associated with computing devices of a healthcare facility, a mobile device 153 associated with one or more caregivers, or by some other notification delivery device.

In some embodiments, the user computing device 151 and the facility computing system 152 may include at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, server device or server system and so forth.

This alarm can be in the form of a message or alarm sent to a hand-held device such as a smartphone of a predetermined caregiver or clinician. The alarm unit can also be configured to send an alarm to the caregivers/nurses in a hospital where the patient is currently being treated. With the help of this alarm, caregivers and/or clinicians are enabled to quickly turn their attention to the patient and intervene in order to prevent and limit more severe complications potentially arising from the seizure.

In some embodiments, the alarm unit 150 may generate an alarm 154 including, e.g., a visual indication via a graphical user interface, an audible indication, a vibration or tactile indication, or other alert notifying the user of the seizure occurrence. In some embodiments, the alarm 154 may be provided to a user computing device 151, movable device 153, facility computing system 152, or other device forming an alarm unit 150, or combinations thereof. For example, the alarm unit 150 may display the visual indication and/or emit the audible, vibration and/or tactile indication such that the caregiver may perceive the alert of the patient’s seizure in real-time with the occurrence of the seizure. As a result, the user may receive a real-time warning of seizures, enabling the user to take preventative or mitigating steps to avoid harm that may result from a seizure.

In some embodiments, the alarm unit 150 may also be embedded in a closed-loop setup linked to a device to administer treatment and thereby lower treat or otherwise mitigate the seizure or prevent it completely. This treatment device may include a system to apply a fast-acting antiseizure medication or a neuromodulatory device which, for example, administers electrical stimulation to the brain in order to decrease seizure risk.

Figure 2:
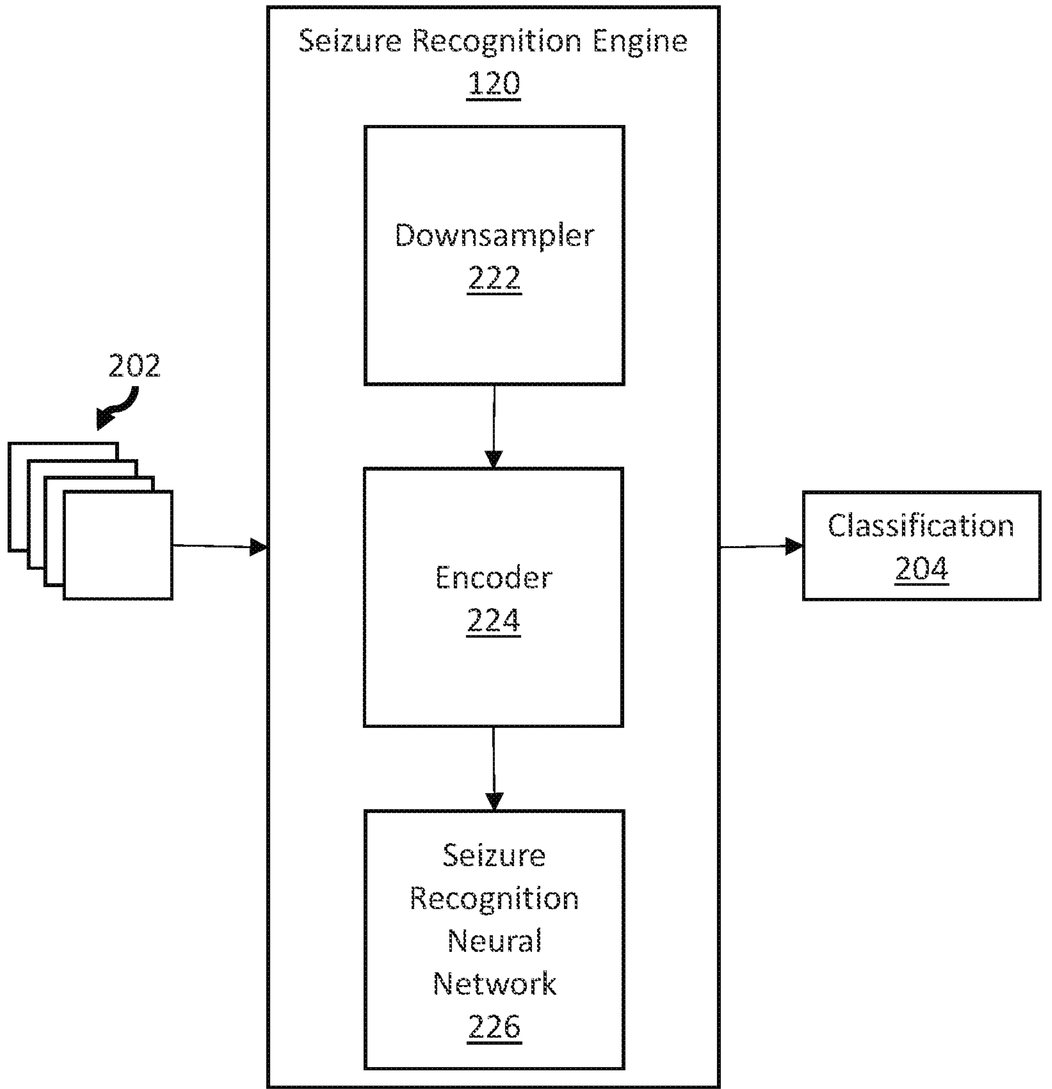
FIG. 2 illustrates an example of a schematic outline of a seizure detection model employed by a system for video-based detection of seizures in accordance with one or more embodiments of the present invention.

FIG. 2 illustrates a block diagram of another exemplary computer-based system and platform including a seizure recognition engine for seizure monitoring and seizure detection in accordance with one or more embodiments of the present disclosure.

In some embodiments, the seizure recognition engine 120 of the processing unit 110 may include components for implementing a seizure recognition neural network 226. In some embodiments, the seizure recognition engine 120 received video data 202 from an epoch of patient monitoring (e.g., a monitoring period preceding a current time) to produce a classification 204 regarding whether the patient is exhibiting seizure signs and symptoms.

In some embodiments, the seizure recognition system 120 utilizes a downsampler 222 to downsample the video data 202 to a uniform format. In some embodiments, a balance between data captured in the video data 202 and processing and storage efficiency and performance may be achieved by Downsampling video frames in the video data 202. For example, the downsample 222 may sample the video data 202 by downsampling frame rates of video sequences, downsampling resolution of each frame of the video data, downsampling color data of each frame of the video data 202, or a combination thereof.

In some embodiments, video clips in the video data 202 may downsampled from an original sample rate or frame rate to a decreased sample rate or frame rate. For example, the downsampler 222 may remove, e.g., every second frame, every third frame, every fourth frame, every fifth frame, or other pattern. In some embodiments, video clips from the video data 202 may include, e.g., 24 Hz, 30 Hz, 60 Hz, 120 Hz, or other sample rate/frame rate. The downsampler 222 may sample frames from the video data 202 to decrease the sample rate/frame rate from the original down to, e.g., 15 Hz, 10 Hz, 5 Hz, 1 Hz, or other decreased sample rate or frame rate, such that sufficient data still remains for recognizing a seizure occurrence, while reducing resource demands.

In some embodiments, the downsampler 222 may downsample each frame of video in the video data 202. For example, the downsample 222 may downsample color data by, e.g., removing color channel data, sampling color channel data, sampling luminance data, among other color data of each frame. For example, the downsampler 222 may reduce the color data of each frame from color to grayscale, thus reducing data and processing requirements while maintaining movement and patient activity information. Similarly, frame resolutions may be downsampled. For example, each frame may be downsampled from an original resolution to, e.g., 720 progressive scan (p) resolution, 480p resolution, 320p resolution, 240p resolution, 720 interlaced (i) resolution, 480i resolution, 320i resolution, 240i resolution, or other reduced resolution sufficient for capturing patient movements and activity while reducing resource demands.

In some embodiments, the downsampled video data may be encoded by an encoder 224 for ingestion by the seizure forecasting neural network 226. In some embodiments, the video data 202 includes a time sequence of video frames. However, to optimize the downsampled video data of downsampled video frames for interpretation by a neural network, the video frames may be encoded to form time-series data. In some embodiments, any suitable encoder 224 techniques for encoding a sequence of video frames into time-series data for use by a neural network may be employed. For example, a pre-trained video encoding neural network, such as, e.g., MobileNet, or other similar network, may be employed. In some embodiments, a network such as MobileNet may be employed without the top layers of the stock MobileNet. However, any suitable video encoding technology may be employed.

In some embodiments, the encoded video data may be processed by a seizure recognition neural network 226 to determine whether patient movements and activity captured by the video data 202 are associated with a seizure occurrence. In some embodiments, the seizure recognition neural network 226 may include, e.g., long short-term memory networks (LSTMs) to encode the temporal sequence of the encoded video data. LSTMs are specifically designed for learning underlying representations in time-series data. However, other neural network architectures may be employed, such as, e.g., gated recovery units (GRU), fully recurrent neural networks, Hopfield networks, bidirectional associative memory, echo state networks, recursive neural networks, recurrent multi-layer perceptron networks, continuous-time neural networks, among others and combinations thereof.

Figure 4A:
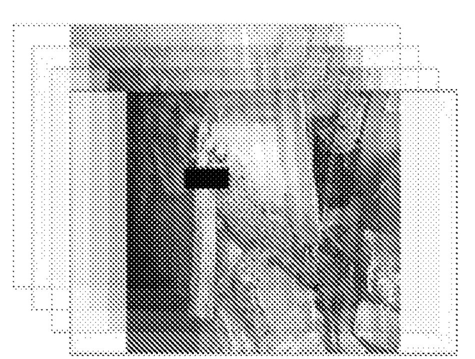
FIGS. 4A and 4B depicts an example of an outline of data processing for automated video seizure detection, in accordance with one or more embodiments of the present invention.
Figure 4A:
Figure 4B:
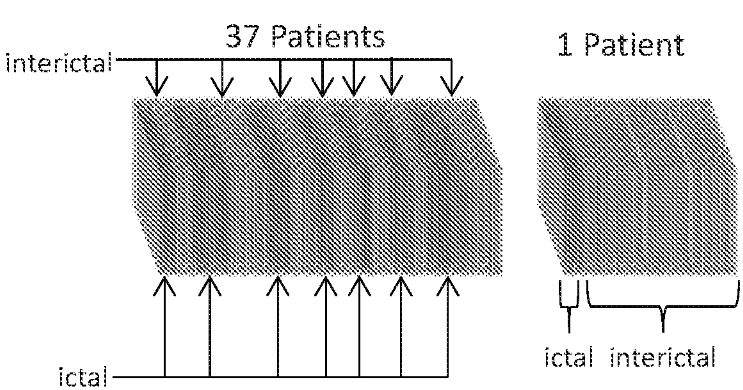

In some embodiments, to limit overfitting, the seizure recognition neural network 226 may be kept simple and shallow (see, FIG. 4C), and training may be performed on matched data where both classes ("seizure" and "no seizure") appear equally often (FIG. 4A, FIG. 4B). However, other techniques for training may be employed. In some embodiments, the seizure recognition neural network 226 may be trained in a supervised fashion, on a set of training sequences (e.g., the matched data), using an optimization algorithm, such as, e.g., gradient descent, combined with backpropagation through time to compute the gradients needed during the optimization process, in order to change each weight of the LSTM network in proportion to the derivative of the error (at the output layer of the LSTM network) with respect to corresponding weight.

In some embodiments, based on the training, the seizure forecasting neural network 226 may ingest the encoded video data and automatically determine a probability of a seizure occurrence captured in the video data 202. As described above, the probability may be a decimal number between 0 and 1. Thus, to produce a classification 204 for the epoch of video data 202, the seizure recognition neural network 226 may compare the seizure probability to a classification threshold. In some embodiments, classification threshold may include a value selected to balance the risks of false positives (an incorrect classification of a seizure occurrence) and false negatives (an incorrect classification no seizure occurrence). In some scenarios, an incorrect determination of "no seizure" may result in patient harm due to lack of care, whereas an incorrect determination of "seizure" may simply result in an unnecessary patient interaction. Thus, due to increased risks of patient harm for false negatives, the classification threshold may be selected to bias towards false positives to limit false negatives. For example, the classification threshold may include a value of about, e.g., 0.4, 0.5, 0.6 or other threshold. As a result, the seizure recognition engine 120 may produce a classification 204 from the video data 202 in real-time whether a patient is experiencing a seizure.

Example—Training an LSTM-Based Seizure Forecasting Model

Figure 3:
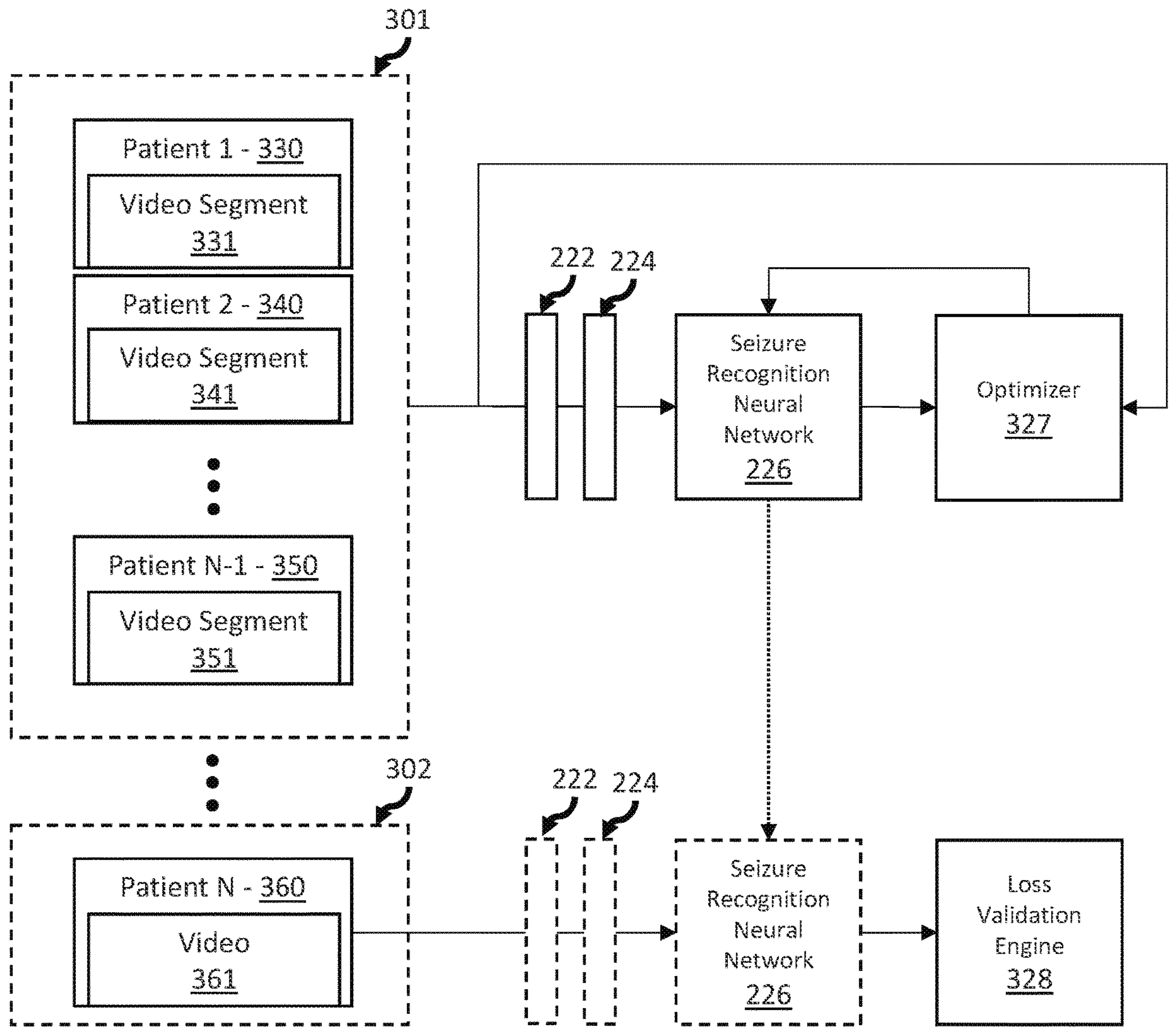
FIG. 3 illustrates an example of a schematic outline of a seizure detection model employed by a system for video-based detection of seizures and the training and testing thereof in accordance with one or more embodiments of the present invention.

FIG. 3 illustrates a block diagram of another exemplary computer-based system and platform including a seizure recognition engine including seizure forecasting neural network training and validation for seizure monitoring and seizure detection in accordance with one or more embodiments of the present disclosure.

Preparation of Training and Test Data

In some embodiments, the video data for training may include recorded videos from epilepsy patients in the EMU. Videos either showed the patient 330, 340 through 350, 360, during normal, non-seizure situations, or during the course of a GTCS. In some embodiments, using the patient training dataset 301, the seizure recognition neural network 226 may be trained by an optimizer 327 to detect the videos during which the patient (330, 340, . . . , 350) experienced a seizure. To validate the training, a loss validation engine 328 may be employed with leave-one-out cross-validation, where matched data from all patients (330, 340, . . . , 350) but one are used for training, with the testing done on all of the data from the remaining out-of-sample patient 360.

In some embodiments, for preparation of the training datasets 301, all video files are separated into consecutive 5-second video segments 331, 341, . . . , 351 and 361. All ictal 5-second segments are including for a patient for training and matched with an equal number of randomly chosen interictal 5-second video segments from the same patient. This matching may mitigate the imbalanced data during training where interictal data often outnumbers ictal data. Next, the matched data from 37 patients of the training dataset 301 may be used for training while testing is performed on the video segment 361 from the remaining patient 360 including the full video segment 361 of both ictal and interictal periods.

Neural Networks and Training

In some embodiments, the video segments 331, 341, . . . , 351 and 361 are downsampled by a downsampler 222 from the original 30 Hz to 10 Hz, turned into grey-scale and resized to 224 times 224 pixel resolution. For encoding of individual video frames a pretrained MobileNet excluding the top layers is employed as an encoder 224. In some embodiments, the seizure recognition neural network 226 may include long short-term memory networks (LSTMs) to encode the temporal sequence of these outputs, as LSTMs are specifically designed for learning underlying representations in timeseries data. To limit LSTMs from overfitting, architectures are kept simple and shallow (FIG. 4C), and training is performed on matched data where both classes appear equally often (FIG. 4A, FIG. 4B).

Performance Metrics

In some embodiments, seizure occurrence detection performance may be assessed with sensitivity, specificity and time in warning. Sensitivity is defined as the fraction of seizures correctly detected, i.e. during which at least one 5-second epoch is classified as ictal. Specificity is defined as the fractions of true negative 5-second epochs during interictal data. Because of its more straight forward clinical interpretability, time in warning is also reported, which is defined as the complement of specificity (e.g., 1-specificity).

Results Show That Our Invention Allows GTC Seizure Detection from Video Only

In some embodiments, the training dataset 301 and testing dataset 302 includes 77 GTC seizures from 38 patients (e.g., age 13.59±4.66, 19 females). For each patient, interictal videos (15.03±3.67 min) are also included, during which patients are either sleeping or engaged in some activity. In an embodiments, a leave-one-out cross-validation approach is employed where patched ictal/interictal video segments 331, 341, . . . , 351 from 37 patients are used for training, and testing is done on the full videos 361 of the one remaining out-of-sample patient 360 (FIG. 4A, FIG. 4B). Seizure detection performance may be evaluated using sensitivity and specificity. FIG. 5 shows the performance for all 38 patients. In an embodiment, five of the 77 seizures were not detected. Across patients a mean sensitivity of 95.18±2.84% and a mean specificity of 81.61±4.46% are reported. The average latency by which a seizure is detected by an embodiment of the seizure recognition neural network 226 after the beginning of the tonic phase is 7.99±2.23 seconds.

In a hospital setting, there are often caretakers and family members approaching the bed and the patient, which may impact the performance of a detection algorithm or potentially confine what the algorithm uses in order to detect a seizure. To determine whether embodiments of the present method would also detect seizures in the absence of any other persons in the video, the times when one or more persons apart from the patient appeared in the video for the first time may be labeled. FIG. 6 shows the time course of seizure likelihood for all patients along with an indication of when other persons appear in the video (black vertical lines). As is evident from this figure, an embodiment of the seizure recognition engine 120 correctly detected the seizure in more than 10% (8/77 seizures) even when no other person was in the video. Thus, a detection mechanism that solely detects a seizure based on whether other persons are visible can be ruled out.

FIG. 4A-4C depicts an example of an outline of data processing for automated video seizure detection, in accordance with one or more embodiments of the present invention. FIG. 4A depicts consecutive ictal video clips of 5 seconds duration (red) were matched with the same number of interictal video clips (green) for each patient, in accordance with one or more embodiments of the present invention. FIG. 4B depicts a leave-one-out cross-validation approach that trained on matched data from all but one patient and evaluated on the full data from the remaining patient was implemented to assess performance, in accordance with one or more embodiments of the present invention. An illustrative network architecture including a learning rate set to 0.001, batch size to 16, Adam optimizer, in accordance with one or more embodiments of the present invention for automated video seizure detection is presented below in Table 1:

TABLE 1

Automated Video Seizure Detection Neural Network Architecture

| Layer Number | Layer Type | Filter/ Kernel Size or Nodes | Layer Parameters |
|---|---|---|---|
| 1 | MobileNet | N/A | Weights-imagenet, include_top = False |
| 2 | Flatten | N/A | N/A |
| 3 | Dropout | N/A | Dropout rate = 0.5 |
| 4 | LSTM | 100 | N/A |
| 6 | Dense | 1 | activation = sigmoid |

Figures 5A, 5B, 5C, 5D:
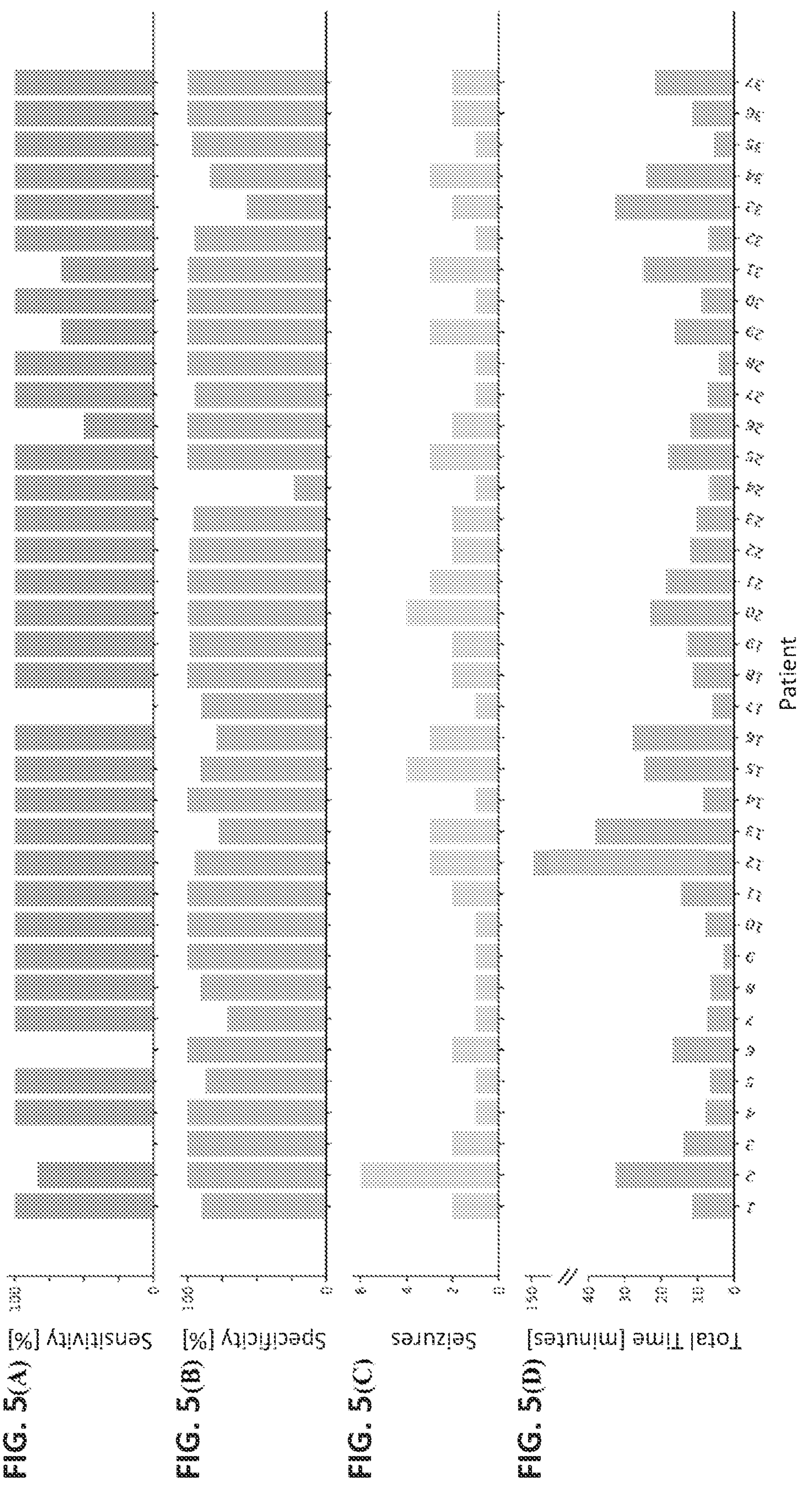
FIGS. 5A-5D depict an example of detection performance results in terms of sensitivity (FIG. 5A), specificity (FIG. 5B) and time in warning (FIG. 5C), with FIG. 5D depicting the number of seizures for each patient, in accordance with one or more embodiments of the present invention.

FIG. 5A-5D depict an example of detection performance results in terms of sensitivity (FIG. 5A), specificity (FIG. 5B) and time in warning (FIG. 5C), with FIG. 5D depicting the number of seizures for each patient, in accordance with one or more embodiments of the present invention.

Figure 6A:
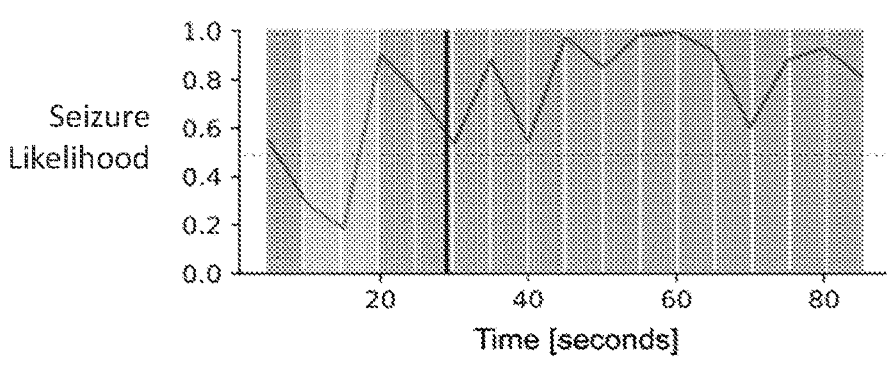
FIGS. 6A-6B depicts an example of a predicted seizure likelihood over the course of each seizure in accordance with one or more embodiments of the present invention.
Figure 6B:
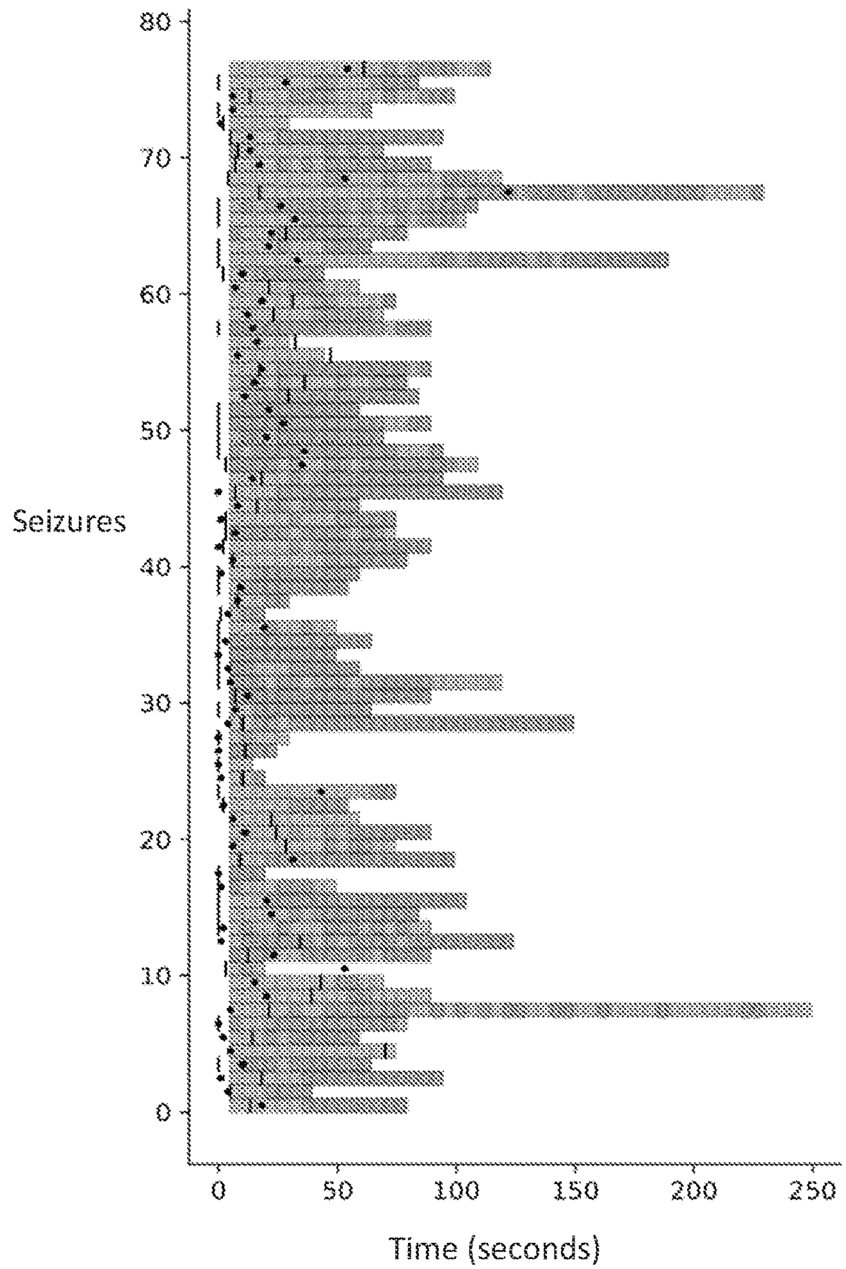

FIG. 6A-6B depicts an example of a predicted seizure likelihood over the course of each seizure in accordance with one or more embodiments of the present invention. FIG. 6A depicts predicted seizure likelihood for one seizure, where likelihood is assessed every 5 seconds; if likelihood is smaller than 0.5 no seizure is detected (light gray), otherwise a seizure is detected during this 5-second epoch (dark gray), in accordance with one or more embodiments of the present invention. FIG. 6B depicts the likelihood time course for all seizures, where black vertical lines indicate the first time another person aside from the patient is visible in the video and black round markers indicate the onset of the tonic phase, in accordance with one or more embodiments of the present invention.

Video-Based Seizure Detection

Figure 7:
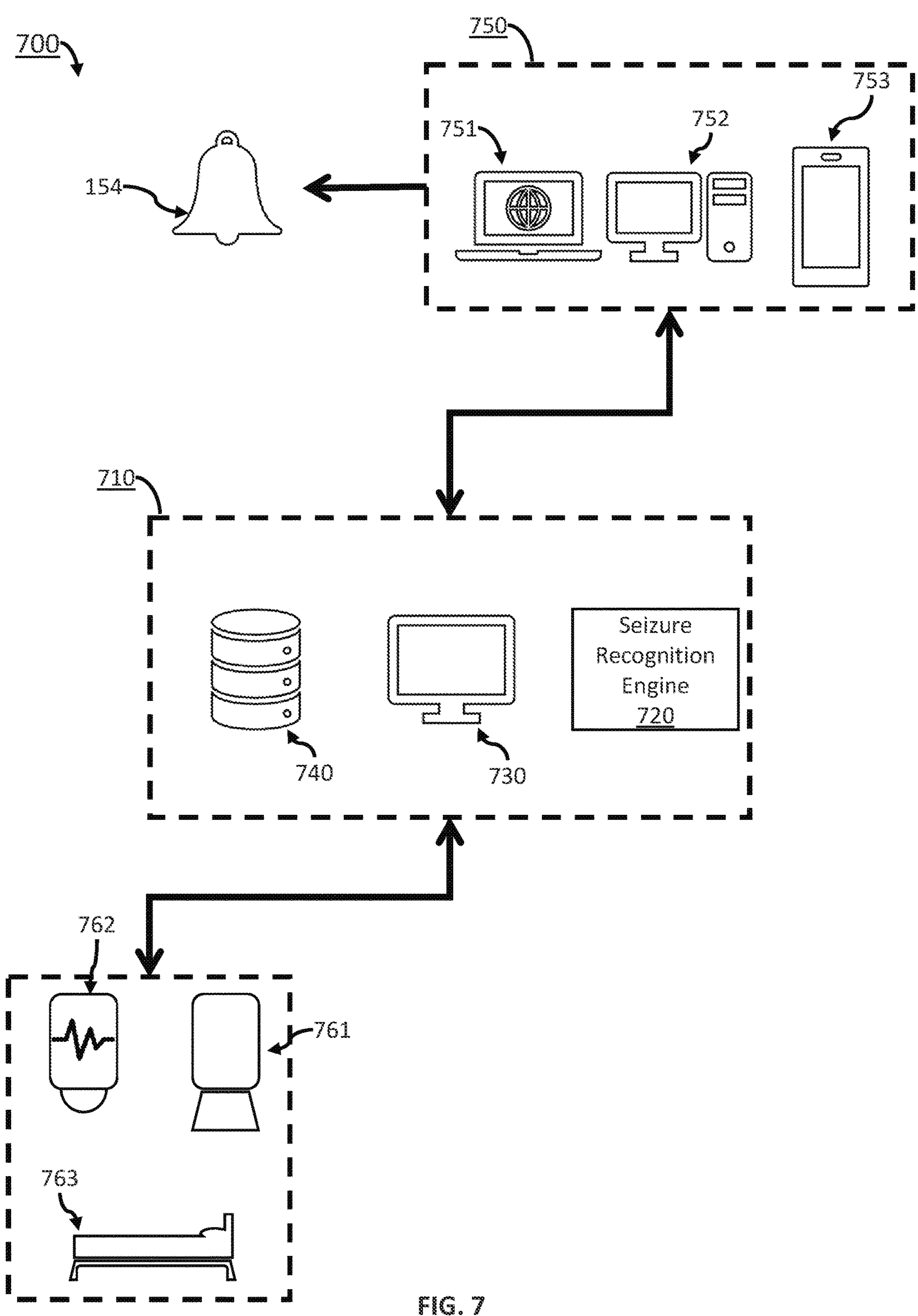
FIG. 7 illustrates an example of a schematic outline of a system for video-based detection of seizures including a video camera unit to record video data of a patient, a data processing unit to determine whether a video shows an epileptic seizure or not, and an alarm unit to provide an alarm once a seizure is detected, in accordance with one or more embodiments of the present invention.

Referring to FIG. 7, an example of a multi-sensor monitoring system 700 for sensor-based seizure detection is illustrated according to embodiments of the present invention.

In some embodiments, a multi-sensor monitoring system 700 may automatically determine whether a patient experiences a seizure using video recordings along with parallel sensor data pipelines, such as, e.g., biometric sensor data from a suitable biometric sensor 762. The multi-sensor monitoring system 700 may include a video capture device 761 to continuously record video of a patient location 763, a biometric sensor 762 to continuously and/or periodically record movement and/or biometrics in the patient location 763, a processing unit 710 to continuously analyze the video data and the biometric sensor data and an alarm unit 750 that provides an alarm 754 when epileptic sensor data is detected.

In some embodiments, the biometric sensor 762 may include a suitable biometric sensor device for continuously or periodically taking biometric sensor-based measurements in the patient location 763. For example, non-contact sensors enable continuous monitoring of a patient that is resistant to patient movement disrupting the non-contact sensor as well as improved patient comfort. Additionally, one or more non-contact sensors and/or the video capture device 761 may be easily combined into a single device, more easily than non-contact sensors. In some embodiments, the biometric sensor 762 may be directed towards or positioned on or near a patient in the patient location 763 to obtain a set of measurements in each biometric sensor sample. In some embodiments, the biometric sensor sample may occur on a suitable interval for a biometric sensor sampling rate to obtain a time-series of biometric measurements. In some embodiments, the biometric sensor 762 may output each sample of measurements, e.g., in an array, vector, waveform, comma-separated values (CSV), and/or may process the measurements to normalize, cleanse, denoise, and/or perform other suitable pre-processing on the biometric sensor data, or in any other suitable format or any combination thereof.

In some embodiments, the biometric sensor 762 may include, e.g., one or more sensors measuring biometric patterns indicative of aspects of seizures. For example, a microphone may be included in the patient location 763 for detecting audio and patient sounds, such as, e.g., respiration sounds and/or vocalizations. Similarly, biometric sensors may include such as, e.g., a photoplethysmography (PPG) sensor, a respiratory rate sensor, a temperature sensor including a body temperature sensor, an electrodermal activity (EDA) sensor, an electroencephalogram (EEG) sensor, an electromyography (EMG) sensor, a near-infrared spectroscopy (NIRS) sensor, synthetic air data system (SADS), among other sensors and devices for measuring the activity of a patient in the patient location 763. In some embodiments, each sensor may be beneficial in facilitating more accurate detection of seizures of different types.

In some embodiments, a biometric sensor 762 may be included to recognize muscle activity. Most seizures have a motor component; therefore, the analysis of muscle activity with a biometric sensor 762 such as sEMG is a viable option for seizure detection. sEMG helps differentiate epileptic seizures from non-epileptic seizures: epileptic seizures have a large proportion of EMG activity in the frequency band above 700-150 Hz. sEMG detects muscle activity with as few as one channel; deltoid and anterior tibialis muscles are the preferred placement sites. Tonic stiffening may include an intense muscle contraction, which allows for early GTCS detection us sEMG and machine learning models. However, disadvantages of sEMG sensors include discomfort when strongly fixed to the skin and potential for detachment. Better results may be achieved when certain parameters are tailored to the individual patient, especially for tonic seizures.

In some embodiments, a biometric sensor 762 may be included to measure skin conductance. Modulation in skin conductance is referred to as EDA, and it reflects the activity of the sympathetic branch of the autonomic nervous system. Sweat increases the conductance of an applied current. In some embodiments, a device applies direct current to the stratum corneum beneath the electrodes and measures the EDA in the ventral side of distal forearms to facilitate the detection of epileptic seizures based on a transiently increased EDA. In some embodiments, therefore, the transient increases in EDA caused by GTCS and focal dyscognitive seizures may be detected to facilitate the detection of seizures. In some embodiments, the change in EDA was higher and remained elevated for a longer period in GTCS compared to focal dyscognitive seizures. In some embodiments, there may be a strong correlation between the duration of postictal generalized EEG suppression (PGES) and the degree of EDA response. Accordingly, EDA recordings may facilitate a better understand the pathophysiology of SUDEP.

In some embodiments, a biometric sensor 762 may be included to measure cardiovascular changes. Cardiovascular changes are relatively easy to measure with a sensor positioned on the patient and/or remotely from the patient. In some embodiments, in patients with epilepsy cardiovascular changes may be particularly relevant as the cardiovascular changes may be linked to SUDEP. In some embodiments, EKG can be recorded from a single channel and has a higher signal to noise ratio than EEG. Heart rate changes may be explained by increased motor activity, release of catecholamines, sympathetic and parasympathetic shifts, activation of limbic structures, increased neuronal firing, or a combination of these and other unknown factors. In some embodiments, heart rate may also depend on the state of vigilance so sensors using heart rate to detect seizures might be affected by this. The pattern of heart rate changes seems to be patient-specific, reflecting the individual spread and evolution of seizure activity. Accordingly, patient-tailored algorithms may be employed with the EKG to facilitate the detection of focal seizures, and, secondarily, generalized seizures and GTCS. In some embodiments, EKG abnormalities may be linearly correlated to electrocorticogram (ECoG) seizure severity, proving the feasibility of EKG as a seizure detection device. In some embodiments, ictal tachycardia may be more prominent when arising from the right hemisphere. In contrast, short myoclonic seizures often do not produce heart changes. Accordingly, an EKG may facilitate accurate detection of focal seizures, tonic-clonic, tonic, clonic and hypermotor seizures. In some embodiments, to facilitate EKG measurement, the EKG monitor may be composed of a wireless sensor board, ultra-low power EKG sensor readout, accelerometer, and micro-secure digital-card. In some embodiments, the EKG monitor may include two electrodes placed on the arm of patients, with a smartphone application or other software to monitor heart rate remotely based on skin color changes.

In some embodiments, since cardiac pulse leads to subtle changes in skin color, a photoplethysmography (PPG) signal can be measured recording from the wrist, or from the face, e.g., with an imaging device such as the video capture device 761 or additional imaging device (e.g., a front facing-camera of a smartphone, separate camera mounted in the patient location 763, etc.). Accordingly, seizures with a motor component may be monitored with this technique. In some embodiments, another option may utilize cardiac-based activation vagus nerve stimulation as part of a closed-loop system. In some embodiments, a cardiac-based seizure detection based on the cardiac-based activation vagus nerve stimulation may improve quality of life.

In some embodiments, accelerometry (ACM) may be employed for the detection of motor seizure as it detects changes in velocity and direction. The signal may be recorded by means of a three-axis motion/accelerometer sensor, a microprocessor, and a small, rechargeable battery, all of which may be placed on a limb. The main challenge is to differentiate seizures from normal, daily, repetitive movements. Some systems have a cancel button, and this gives the opportunity to indicate that a movement was a false alarm, avoiding a false-positive alert to the caregiver. In some embodiments, such a modality may detect focal seizures with minimal motor component, GTCS, secondarily generalized seizures, myoclonic, clonic, tonic and hypermotor seizures. Clonic seizures present with a burst-like pattern, which was better identified and discriminated from other movements. Tonic seizures are block-shaped because the acceleration is almost constant. Tonic seizures resemble slow normal movements, which makes them harder to identify. Focal dyscognitive seizures without motor phenomena and absence seizures may be difficult to detect with ACM.

In some embodiments, an automatic video detection system may use velocity, area, duration, rotation, oscillation, angular speed, and/or displacement (motion trajectory) to detect seizures based on changes in position and pose of the patient and/or body parts of the patient in the patient location 763. The underlying concept is to detect complex motor patterns by automatic interpretation of video data. In some embodiments, automatic video detection may include as marker-based or marker-free types of detection, depending on whether the cameras track detectable markers placed in relevant places. In some embodiments, automatic video detection may detect seizure types such as focal, hypermotor, myoclonic, and clonic. Myoclonic seizures are detected with good sensitivity and specificity with a marker-based system using spatio-temporal interest points. Reference markers may be placed on the head, trunk and extremities to assess for movement when evaluated with infrared light by a video system. In some embodiments, marker-based devices present with the shortcoming that sensors can be uncomfortable or dislocate over time. In some embodiments, marker-free systems detect seizures with a motor component but may have difficulty in detecting seizures without a motor component and may be more limited to the area covered by video: the patient must be visible and properly placed. Seizure detection based on video is feasible, but it recognizes mainly seizures with large movements.

In some embodiments, a mattress sensors may be employed to detect GTCS, which may be particularly beneficial for preventing SUDEP while a patient is unsupervised in bed at night. In some embodiments, the mattress sensor may include a sensor placed under the patient's mattress and connected to a monitor. The sensor alerts the caregiver when it detects a stimulus above the set threshold including, e.g., movement, noise frequency and intensity or other behavior or any combination thereof. In some embodiments, the mattress sensor may be adjusted for individual differences by calibrating sensor parameters.

In some embodiments, increased cerebral blood flood may precede the onset of a clinical seizure in temporal lobe epilepsy. Accordingly, in some embodiments, the biometric sensor 762 may include a sensor for measuring the cerebral blood flood, such as, e.g., transcutaneous regional cerebral oxygen saturation (rSO2) sensors, e.g., on each side of the forehead may detect such increases in cerebral blood flood. For example, increases in the mean rSO2 value, e.g., by 3 standard deviations, or other suitable increase, may indicate an increase in cerebral blood flood that is associated with an impending GTCS seizure.

In some embodiments, wavelengths used in near-infrared spectroscopy (NIRS) may measure cerebral oxygen saturation by using the absorption properties of tissues in the near-infrared range with or without contact with the patient and without invasive procedures. Accordingly, in some embodiments, the biometric sensor 762 may include, e.g., a spectrophotometer placed on the patient (e.g., on the forehead, the wrist, a finger, etc.) and emit light into the tissue from the surface of the skin, and then collect the light from a detector close to the emitter. In some embodiments, seizures analyzed with this approach may include seizures mainly including focal, including focal dyscognitive, including focal without impairment of consciousness, including focal with secondary generalization or any combination thereof and/or an absence seizures. In some embodiments, the NIRS spectrophotometer in temporal lobe seizures may detect an increase in rSO2 in the preictal period, followed by a decline around seizure onset, and then a postictal increase. In some embodiments, the frontal generalized spike and wave discharges may be associated with moderate oxygenation before the discharge, followed by a deoxygenation, then a second increase in oxygenation, and a return to baseline.

In some embodiments, an implanted advisory system may be employed to predict and quantify seizures in adults with refractory focal seizures. In some embodiments, two silicon leads, each with, e.g., eight contacts, may be placed over the quadrant with the epileptogenic zone to detect seizures using a patient-specific algorithm.

In some embodiments, skin temperature may be correlated with the occurrence or impending occurrence of a seizure, and may be related to seizure type. Accordingly, in some embodiments, the biometric sensor 762 may include, e.g., a temperature sensor, such as an infrared temperature sensor and/or contact thermometer or any combination thereof. In some embodiments, skin temperature may be monitored to indicate impending seizures. For example, the ratio of mean temperature during sleep and awake periods may be related to seizures, e.g., in the following day. Accordingly, the biometric sensor 762 may include a wristband or other wearable sensor for monitoring skin temperature.

In some embodiments, cardiac and respiratory abnormalities may be a cause for SUDEP. Accordingly, in some embodiments, a device to monitor chest and abdominal excursion by respiratory inductance plethysmography may be employed to detect ictal apnea to identify and/or predict temporal lobe seizures.

In some embodiments, the biometric sensor 762 may be employed to use wave transmission to identify motion caused, for example, by a change in the patient's position in bed. In some embodiments, the combination of biometric sensor, video and ACM may increase the ability to detect seizures.

In some embodiments, seizures may cause identifiable combinations of biometric activity in an individual. Accordingly, in some embodiments, multiple sensors may be combined in the biometric sensor 762 for multi-sensor-based measurements that are configured to identify the combinations of biometric activity that indicate a seizure or impending seizure. For example, in some embodiments, the biometric sensor 762 may include, e.g., an EDA and an ACM biosensor, e.g., placed on a forearm of a patient. The combination of EDA and ACM measurements may improve the detection of seizures during awake and sleep states.

Similarly, in some embodiments, sEMG and ACM may be included in the biometric sensor 762 to enhance detection of seizures with motor and autonomic system involvement because ACM seems to be more sensitive in detecting the clonic phase, and sEMG the tonic phase of seizures.

Additionally, or alternatively, a magnetometer may be combined with an ACM sensor in the biometric sensor 762. In some embodiments, the magnetometer may be used as a seizure detection sensor because the magnetometer characterizes movement in the horizontal plane, as seen in a tonic seizure by measuring body inclination using a 3D Earth's magnetic field sensor and track changes in orientation in 3D space. In some embodiments, the combination of magnetometer and ACM may include three sensor modules, each including a tri-axial ACM and a tri-axial magnetometer, positioned in contact with the patient, e.g., on the head and both wrists of patients. In some embodiments, the sensors discriminate tonic activity, clonic activity, hypermotor movements, and no movements for improved seizure detection. In some embodiments, the biometric sensor 762 may include any suitable combination of sEMG, ACM, magnetometers, gyroscopes, or other biometric sensor devices to improve seizure detection through the combination of detected biometrics.

In some embodiments, the processing unit 710 may include any type of data processing capacity, such as a hardware logic circuit, for example an application specific integrated circuit (ASIC) and a programmable logic, or such as a computing device, for example, a microcomputer or microcontroller that include a programmable microprocessor. In some embodiments, the processing unit 710 may include data-processing capacity provided by the microprocessor. In some embodiments, the microprocessor may include memory, processing, interface resources, controllers, and counters. In some embodiments, the microprocessor may also include one or more programs stored in memory.

In some embodiments, the processing unit 710 may be a part of a computing device associated with the patient, a caregiver of the patient, a family member of the patient, a healthcare facility or service associated with the patient or where the patient location 763 is located, among other related systems responsible for monitoring health of the patient. In some embodiments, the processing unit 710 may embodied is a user computer, laptop computer, mobile computing device, server or server system, cloud computing system, or other computing system.

In some embodiments, the processing unit 710 may include a database 740 for receiving and storing the video from the video capture device 761 and the biometric sensor data from the biometric sensor 762. In some embodiments, the database 740 may be configured to maintain a record of the video for a predetermined period of time, e.g., about a week, a month, 3 months, 6 months, a year, or other length of time. Similarly, in some embodiments, the database 740 may be configured to maintain a record of the biometric sensor data for a predetermined period of time, e.g., about a week, a month, 3 months, 6 months, a year, or other length of time. As such, the database 740 may provide video data and biometric sensor data related to a patient for a period of time to allow a user to review the data, to update or train seizure recognition models of the seizure recognition engine 720, among other uses. As such, the length of time may be any suitable length of time to review the data, update the models, or any other use, subject to the pertinent patient privacy requirements (e.g., HIPPA or other laws and standards).

In some embodiments, the database 740 may be configured to communicate with the seizure recognition engine 720. Accordingly, the seizure recognition engine 720 may ingest data from the database 740 for training and updating seizure recognition models, based on known outcomes for segments of video data and/or segments of the biometric sensor data. In some embodiments, the video data and/or biometric sensor data in the database 740 may also be used to test and evaluation predictions by the seizure recognition engine 720.

In some embodiments, the database 740 may include, e.g., a suitable memory or storage solutions for providing electronic data to the processing unit 710. For example, the database 740 may include, e.g., a centralized or distributed database, cloud storage platform, decentralized system, server or server system, among other storage systems, or the database 740 may include, e.g., a hard drive, solid-state drive, flash drive, or other suitable storage device, or the data storage 712 may include, e.g., a random access memory, cache, buffer, or other suitable memory device, or any other data storage solution and combinations thereof.

In some embodiments, the database 740 may receive and record the continuous stream of the video data and the biometric sensor data among other patient data, including electronic medical record data, clinical data, radiological and other imagery and test results, medication and medication dosages, patient height, patient weight, patient age, patient gender/sex, and any other health-related data, such as any data from an electronic medical health record or other health record. The video data and/or biometric sensor data may be accessible by, e.g., seizure recognition engine 720, a user terminal 730 and the alarm unit 750. However, in some embodiments, the video data and/or biometric sensor data may be provided directly to the seizure recognition engine 720 and the alarm unit 750 before or instead of being stored in the database 740.

In some embodiments, during patient monitoring, the seizure recognition engine 720 may receive video data as a direct feed from the video capture device 761, or indirectly via the database 740, so long as the video data is provided to the seizure recognition engine 720 quickly enough to identify any seizure signs and symptoms and communicate the determination to the alarm unit 750 for alerting a caregiver in time to mitigate hazards associated with a seizure. Accordingly, in some embodiments, video is recorded in real-time with a video-capture device 761 and sent to the data processing unit 710. In the processing unit 710, the video data is continuously evaluated and automatically classified as either "seizure" or "no seizure" using the seizure recognition engine 720.

In some embodiments, during patient monitoring, the seizure recognition engine 720 may receive biometric sensor data as a direct feed from the biometric sensor 762, or indirectly via the database 740, so long as the biometric sensor data is provided to the seizure recognition engine 720 quickly enough to identify any seizure signs and symptoms and communicate the determination to the alarm unit 750 for alerting a caregiver in time to mitigate hazards associated with a seizure. Accordingly, in some embodiments, biometric sensor is recorded in real-time with the biometric sensor 762 and sent to the data processing unit 710. In the data processing unit 710, the biometric sensor data is continuously evaluated and automatically classified as either "seizure" or "no seizure" using the seizure recognition engine 720. In some embodiments, the data processing unit 710 may analyze raw data from the biometric sensor 762 and provide the segments of the raw data to the seizure recognition engine 720 for classification. In some embodiments, the data processing unit 710 and/or the biometric sensor 762 may instead identify particular signatures in the biometric sensor data, such as, e.g., breaths, pulse, cardiac activity spikes, EDA spikes, PPG spikes, or other changes in biometric sensor patterns or other bodily movements or any combination thereof.

In some embodiments, the video data and the biometric sensor data along with the additional patient data may be ingested by the seizure recognition engine 720 for classification as parallel data streams. Accordingly, the data processing unit 710 may extract segments from each of the video data and the biometric sensor data to produce input sequences of each of the video data and biometric sensor data. In some embodiments, each input sequence may include feature vectors and/or feature maps for each frame of video in the sequence and a time series of measurements the biometric sensor data. In some embodiments, the time-series of the biometric sensor data and the frames of the video data may be combined into a single feature vector and/or feature map for each timestamp in the sequence or may be separated into individual respective feature vectors and/or feature maps for each timestamp in the sequence.

For example, in some embodiments, at each timestamp in a period of time, the biometric sensor 762 readings and the frame of video from the video capture device 761 may be quantified as input features and appended to a feature vector and/or feature map. For example, a feature map for each video frame at each time stamp may be created using the pixel values of each pixel in each video frame. Similarly, for a measurement or set of measurements at the timestamp from the biometric sensor 762 may be used to create a vector of the measurement or set of measurements at that timestamp. The vector of the measurement or set of measurements may then be appended to the feature map of the video frame(s) at the timestamp and provided to the seizure recognition engine 720. Alternatively, the feature map for the video frame(s) and the vector of the measurement or set of measurements may be provided as separate inputs to the seizure recognition engine 720. An additional feature vector including the patient data may be also be provided along with the feature map for the video frame(s) and the vector of the measurement or set of measurements, either as appended portions of the feature map, or as a separate feature vector.

In some embodiments, the seizure recognition engine 720 includes a combination of hardware and/or software for inferring a seizure occurrence in real-time based on the video data, or a subset of the video data pertaining to a selected segment of time preceding a current time. In some embodiments, the seizure recognition engine 720 may determine the presence of a seizure occurrence continuously (e.g., using a continuous feed of video data continuously processed with models, e.g., using a rolling time window of video data) or periodically, e.g., once every detection period using a monitoring period of video data. In some embodiments, the detection period may be, e.g., every second, every ten seconds, every fifteen seconds, every twenty seconds, every thirty seconds, every minute, or other suitable period to detect a seizure occurrence in time to notify a caregiver to mitigate hazards. Thus, for each detection period, the seizure recognition engine 720 may develop a seizure occurrence determination for that detection period based on video data and biometric sensor measurements of a monitoring period and other health-related data. In some embodiments, the monitoring period may include video data and biometric sensor measurements from a suitable period of time for identifying a seizure occurrence, such as, a time window of about, e.g., five second epochs, 10 second epochs, 15 second epochs, 20 second epochs, 30 second epochs, or other time window duration.

In some embodiments, the seizure recognition engine 720 may process each epoch of video data and biometric sensor measurements to determine whether each epoch includes a seizure occurrence. In some embodiments, the seizure recognition engine 720 may employ machine learning models and techniques trained to detect seizure occurrences based on epochs of the video data in tandem with biometric sensor measurements. Thus, in some embodiments, the seizure recognition engine 720 may include a machine learning model for differentiating between video combined with biometric measurements of patient activity that indicates "seizure" and video combined with biometric measurements of patient activity that indicates "no seizure." To do so, in some embodiments, the seizure recognition engine 720 may include artificial intelligence (AI) or machine learning techniques for generating a binary classification of an epoch of data at each detection period based on the epoch of video data and biometric sensor measurements and, e.g., physiological parameters and physiological data from, e.g., electronic medical health records. In some embodiments, the machine learning models and techniques of the seizure recognition engine 720 may include techniques chosen from, but not limited to, classifiers such as, e.g., decision trees, boosting, support-vector machines, neural networks, nearest neighbor algorithms, Naive Bayes, bagging, random forests, and the like. In some embodiments and, optionally, in combination of any embodiment described above or below, an exemplary neutral network technique may be one of, without limitation, feedforward neural network, radial basis function network, recurrent neural network, convolutional network (e.g., U-net), long short-term memory network or other suitable network. In some embodiments and, optionally, in combination of any embodiment described above or below, an exemplary implementation of Neural Network may be executed as follows:

a. define Neural Network architecture/model,
b. transfer the input data to the exemplary neural network model,
c. train the exemplary model incrementally,
d. determine the accuracy for a specific number of timesteps,
e. apply the exemplary trained model to process the newly-received input data,
f. optionally and in parallel, continue to train the exemplary trained model with a predetermined periodicity.

In some embodiments and, optionally, in combination of any embodiment described above or below, the exemplary trained neural network model may specify a neural network by at least a neural network topology, a series of activation functions, and connection weights. For example, the topology of a neural network may include a configuration of nodes of the neural network and connections between such nodes. In some embodiments and, optionally, in combination of any embodiment described above or below, the exemplary trained neural network model may also be specified to include other parameters, including but not limited to, bias values, functions and aggregation functions. For example, an activation function of a node may be a step function, sine function, continuous or piecewise linear function, sigmoid function, hyperbolic tangent function, or other type of mathematical function that represents a threshold at which the node is activated. In some embodiments and, optionally, in combination of any embodiment described above or below, the exemplary aggregation function may be a mathematical function that combines (e.g., sum, product, etc.) input signals to the node. In some embodiments and, optionally, in combination of any embodiment described above or below, an output of the exemplary aggregation function may be used as input to the exemplary activation function. In some embodiments and, optionally, in combination of any embodiment described above or below, the bias may be a constant value or function that may be used by the aggregation function and/or the activation function to make the node more or less likely to be activated.

As used herein, the terms "engine", such as the seizure recognition engine 720, identifies at least one software component or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Computer-related systems, computer systems, and systems, as used herein, include any combination of hardware and software. Examples of software may include software components, programs, applications, operating system software, middleware, firmware, software modules, routines, subroutines, functions, methods, procedures, software interfaces, application program interfaces (API), instruction sets, computer code, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, the classification from the seizure recognition engine 720 can include a binary classification (e.g., "seizure" or "no seizure"). The binary classification can include a probability that at a given detection period the epoch of data (e.g., video data and biometric sensor data) shows patient activity associated with a seizure occurrence as opposed to other activities, movements, etc. including other paroxysmal events. For example, the classification may include a numerical value on a scale from 0 to 1, where 0 indicates a zero percent probability of a seizure occurrence in the epoch of data, and where 1 indicates a one hundred percent probability of a seizure occurrence in the epoch of data. In practice, any given prediction period is unlikely to be a 0 or a 1, but likely may be classified somewhere in between. Thus, in some embodiments, the seizure recognition engine 720 may determine a classification for an epoch of data based on, e.g., a classification threshold. For example, where the probability rises above a classification threshold of, e.g., 0.5, 0.52, 0.54, 0.56, 0.58, 0.6, the seizure recognition engine 120 may determine that the epoch of data includes patient activity including a seizure occurrence. This process may be repeated for each subsequent epoch of data generated and received to continuously monitor for seizure occurrence.

In some embodiments, once a seizure is detected (i.e. data is classified as "seizure"), the connected alarm unit 750 triggers an alarm 754 via a notification device, such as, e.g., a user computing device 751 associated with one or more caregivers of the patient, a facility computing system 752 associated with computing devices of a healthcare facility, a mobile device 753 associated with one or more caregivers, or by some other notification delivery device.

In some embodiments, the user computing device 751 and the facility computing system 752 may include at least one personal computer (PC), laptop computer, ultra-laptop computer, tablet, touch pad, portable computer, handheld computer, palmtop computer, personal digital assistant (PDA), cellular telephone, combination cellular telephone/PDA, television, smart device (e.g., smart phone, smart tablet or smart television), mobile internet device (MID), messaging device, data communication device, server device or server system and so forth.

This alarm can be in the form of a message or alarm sent to a hand-held device such as a smartphone of a predetermined caregiver or clinician. The alarm unit 750 can also be configured to send an alarm to the caregivers/nurses in a hospital where the patient is currently being treated. With the help of this alarm, caregivers and/or clinicians are enabled to quickly turn their attention to the patient and intervene in order to prevent and limit more severe complications potentially arising from the seizure.

In some embodiments, the alarm unit 750 may generate an alarm 754 including, e.g., a visual indication via a graphical user interface, an audible indication, a vibration or tactile indication, or other alert notifying the user of the seizure occurrence. In some embodiments, the alarm 754 may be provided to a user computing device 751, movable device 753, facility computing system 752, or other device forming an alarm unit 750, or combinations thereof. For example, the alarm unit 750 may display the visual indication and/or emit the audible, vibration and/or tactile indication such that the caregiver may perceive the alert of the patient's seizure in real-time with the occurrence of the seizure. As a result, the user may receive a real-time warning of seizures, enabling the user to take preventative or mitigating steps to avoid harm that may result from a seizure.

In some embodiments, the alarm unit 750 may also be embedded in a closed-loop setup linked to a device to administer treatment and thereby lower treat or otherwise mitigate the seizure or prevent it completely. This treatment device may include a system to apply a fast-acting antiseizure medication or a neuromodulatory device which, for example, administers electrical stimulation to the brain in order to decrease seizure risk.

Figure 8:
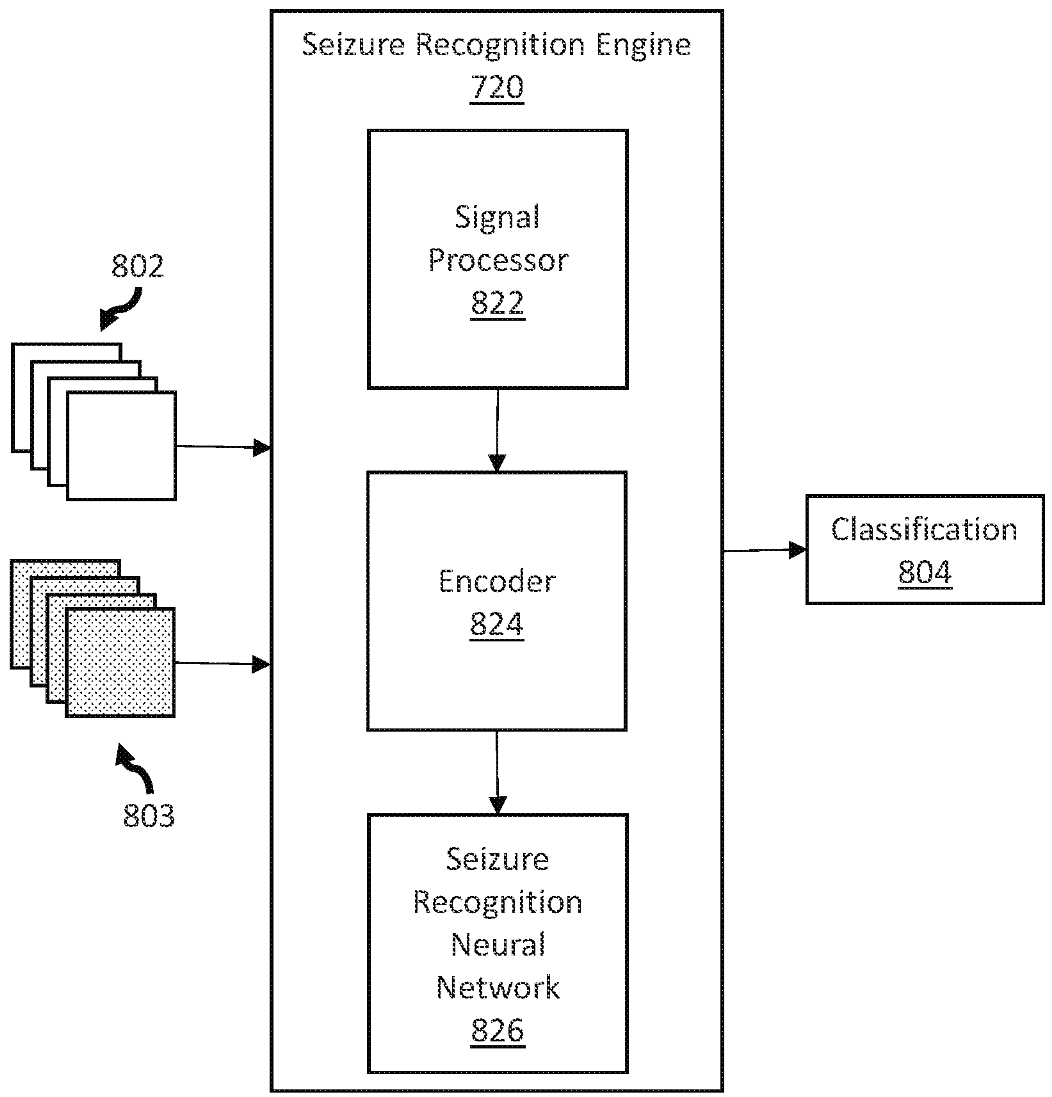
FIG. 8 illustrates an example of a schematic outline of a seizure detection model employed by a system for sensor-based detection of seizures in accordance with one or more embodiments of the present invention.

FIG. 8 illustrates a block diagram of another exemplary computer-based system and platform including a seizure recognition engine for seizure monitoring and seizure detection in accordance with one or more embodiments of the present disclosure.

In some embodiments, the seizure recognition engine 120 of the processing unit 110 may include components for implementing a seizure recognition neural network 826. In some embodiments, the seizure recognition engine 120 receives video data 802 and biometric sensor data 803 from an epoch of patient monitoring (e.g., a monitoring period preceding a current time) to produce a classification 804 regarding whether the patient is exhibiting seizure signs and symptoms. In some embodiments, the video data 802 and the biometric sensor data 803 may be paired with additional clinical factors, such as, e.g., age, sex, age of seizure onset, etiology, seizure type, and semiology, seizure localization, seizure frequency, and medical comorbidities; there are also triggers of seizures, most prominently light stimulation, sleep deprivation, alcohol intake/withdrawal (seizures are most prominent when the alcohol level drops), hyperventilation, or ambient factors or any combination thereof.

In some embodiments, the seizure recognition engine 120 utilizes a signal processor 822 to process the video data 802 to a uniform format of video frames and process the biometric sensor data 803 to a uniform format of biometric sensor measurement samples. In some embodiments, a balance between detail, resource efficiency and performance may be achieved by, e.g., downsampling video frames in the video data 802. For example, the signal processor 822 may sample the video data 802 by downsampling frame rates of video sequences, downsampling resolution of each frame of the video data, downsampling color data of each frame of the video data 802, or a combination thereof.

In some embodiments, sequences of video frames in an epoch of the video data 802 may downsampled from an original sample rate or frame rate to a decreased sample rate or frame rate. For example, the signal processor 822 may remove, e.g., every second frame, every third frame, every fourth frame, every fifth frame, or other pattern. In some embodiments, video clips from the video data 802 may include, e.g., 24 Hz, 30 Hz, 60 Hz, 120 Hz, or other sample rate/frame rate. The signal processor 822 may sample frames from the video data 802 to decrease the sample rate/frame rate from the original down to, e.g., 15 Hz, 10 Hz, 5 Hz, 1 Hz, or other decreased sample rate or frame rate, such that sufficient data still remains for recognizing a seizure occurrence, while reducing resource demands.

In some embodiments, the signal processor 822 may downsample each frame of video in the video data 802. For example, the signal processor 822 may downsample color data by, e.g., removing color channel data, sampling color channel data, sampling luminance data, among other color data of each frame. For example, the signal processor 822 may reduce the color data of each frame from color to grayscale, thus reducing data and processing requirements while maintaining movement and patient activity information. Similarly, frame resolutions may be downsampled. For example, each frame may be downsampled from an original resolution to, e.g., 720 progressive scan (p) resolution, 480p resolution, 320p resolution, 240p resolution, 720 interlaced (i) resolution, 480i resolution, 320i resolution, 240i resolution, or other reduced resolution sufficient for capturing patient movements and activity while reducing resource demands.

Similarly, in some embodiments, the signal processor 822 may process the biometric sensor data 803 to balance detail with resource efficiency. For example, the biometric sensor 762 may take biometric sensor measurements at a predetermined sweep repetition rate, such as, e.g., 1 Hz, 5 Hz, 10 Hz, 15 Hz, 20 Hz, 25 Hz, 30 Hz, 50 Hz, 60 Hz, 75 Hz, 100 Hz, or other suitable sample rate. Accordingly, the biometric sensor data 203 may include, e.g., a data sample rate of, e.g., 1 Hz, 5 Hz, 10 Hz, 15 Hz, 20 Hz, 25 Hz, 30 Hz, 50 Hz, 60 Hz, 75 Hz, 100 Hz, or other suitable sample rate.

In some embodiments, biometric sensor measurement segments in the biometric sensor data 803 may be downsampled from the sensor sampling rate to a decreased sample rate. For example, the signal processor 822 may remove, e.g., every second measurement, every third measurement, every fourth measurement, every fifth measurement, or other pattern. For example, the signal processor 822 may sample measurements from the biometric sensor data 803 to decrease the sample rate from the sensor sample rate down to, e.g., 15 Hz, 10 Hz, 5 Hz, 1 Hz, or other decreased sample rate, such that sufficient data still remains for recognizing a seizure occurrence, while reducing resource demands.

In some embodiments, the biometric sensor 762 may generate two-dimensional data, such as, e.g., spatial infrared, magnetism, sonar, or other spatial measurements. Thus, the biometric sensor 762 may output a two dimensional array of measurements. In some embodiments, the signal processor 822 may downsample a two dimensional array of biometric sensor measurements in the biometric sensor data 803. For example, array size may be downsampled. For example, each array may be downsampled from an original size based on the biometric sensor 762 sensitivity to a size corresponding to the resolution of each frame of the downsampled video frames, e.g., 720 progressive scan (p) resolution, 480p resolution, 320p resolution, 240p resolution, 720 interlaced (i) resolution, 480i resolution, 320i resolution, 240i resolution, or other reduced resolution sufficient for capturing patient movements and activity while reducing resource demands. Thus, each time stamp of biometric sensor data 803 may include a two dimensional array of biometric sensor measurements that has a size that is analogous to, e.g., 720 progressive scan (p) resolution, 480p resolution, 320p resolution, 240p resolution, 720 interlaced (i) resolution, 480i resolution, 320i resolution, 240i resolution, or other resolution.

Alternatively, or in addition, in some embodiments, the signal processor 822 may process the biometric sensor data 803 by, e.g., analyzing the biometric sensor measurement segments of the biometric sensor data 803 for movements performed by a person, such as, e.g., breathing, pulse, limb or other bodily movement, among other data. For example, in some embodiments, the signal processor 822 may include, e.g., a respiration detection model to analyze a time-series of the biometric sensor data 803 to identify breathing motions (e.g., using accelerometer, NIRS, video frames, mattress sensors, etc.), e.g., by outputting a time-series of respiration statuses and/or measurements, and/or a respiration detection model to analyze a time-series of the biometric sensor data 803 to calculate an inferred respiration rate based on heart rate and blood flow as measured by a PPG signal, or by any other suitable respiration detection technique or any combination thereof. In another example, in some embodiments, the signal processor 822 may include, e.g., a pulse detection model to analyze a time-series of the biometric sensor data 803 and/or video data 802 and identify heart rate-related motions, e.g., by outputting a time-series of pulse measurements. In another example, in some embodiments, the signal processor 822 may include, e.g., a tremor detection model to analyze a time-series of the biometric sensor data 803 and/or video data 802 and identify bodily motions indicate of a tremor, e.g., by outputting a time-series of tremor measurements for each body part.

As a result, in some embodiments, the signal processor 822 may output sensor data including downsampled sequences of video frames from the video data 802 and processed biometric sensor data 803 such as downsampled biometric sensor data 803 and/or movement measurements from the biometric sensor data 803.

In some embodiments, the sensor data may be encoded by an encoder 824 for ingestion by the seizure forecasting neural network 826. In some embodiments, the sensor data includes a time sequence of video frames, biometric sensor measurement arrays, and/or movement measurements. In some embodiments, the signal processor 822 may perform a synchronization of the time-series produced by each sensor, including the biometric sensor data 803 and the video data 802. In some embodiments, the biometric sensor data 803 may include time-stamped sensor measurements and/or periodic time markers in the biometric sensor data 803 recordings. Similarly, the video data 802 may include time-stamped video frames and/or periodic time markers in the video data 802 recordings. Accordingly, the signal processor 822 may align the time-stamps and/or time markers, e.g., by aligning segments following each time marker or by any other suitable mathematical alignment process, in order to synchronize the video data 802 and the biometric sensor data 803 in time.

Furthermore, to optimize the sensor data for interpretation by a neural network, the sensor data may be encoded to form time-series data. In some embodiments, any suitable encoder 824 techniques for encoding a sequence of sensor data into time-series data for use by a neural network may be employed. For example, a pre-trained image encoding neural network, such as, e.g., MobileNet, or other similar network, e.g., pre-trained for movement detection and/or classification, may be employed to encode each image and/or each frame of video. In some embodiments, an additional or alternative neural network may be employed for encoding and/or analyzing video, e.g., as a temporal sequence of encoded frames or a sequence of non-encoded frames. In some embodiments, a network such as MobileNet or a network trained on activity detection for another application, may be employed with or without its top layers. However, any suitable video, image or generally activity classification encoding technology may be employed. In another example, a pre-trained biometric sensor measurement encoding neural network, such as, e.g., MobileNet, or other similar network, may be employed and/or adapted. In some embodiments, a network such as MobileNet may be employed without the top layers of the stock MobileNet to be then further trained for seizure detection in a transfer learning approach. However, any suitable video or image encoding technology may be employed to encode a video directly and/or to encode frames of the video and then analyze the encoded frames as a temporal sequence, or any suitable combination thereof. In some embodiments, the encoding technology may be pre-trained and potentially be further adapted to seizure detection using further training, including transfer learning.

In some embodiments, the encoded data may be processed by a seizure recognition neural network 826 to determine whether patient movements and activity captured by the video data 802 and biometric sensor data 803 are associated with a seizure occurrence. In some embodiments, the seizure recognition neural network 826 may include, e.g., long short-term memory networks (LSTMs) to encode the temporal sequence of the encoded data. LSTMs are specifically designed for learning underlying representations in time-series data. However, other neural network architectures may be employed, such as, e.g., gated recovery units (GRU), fully recurrent neural networks, Hopfield networks, bidirectional associative memory, echo state networks, recursive neural networks, recurrent multi-layer perceptron networks, continuous-time neural networks, among others and combinations thereof.

Figure 10A:
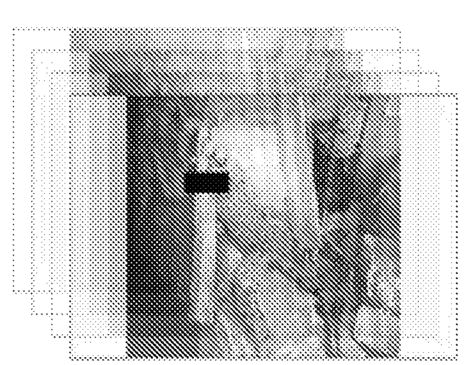
FIG. 10A and FIG. 10B depicts an example of an outline of data processing for automated sensor-based seizure detection, in accordance with one or more embodiments of the present invention.
Figure 10A:
Figure 10B:
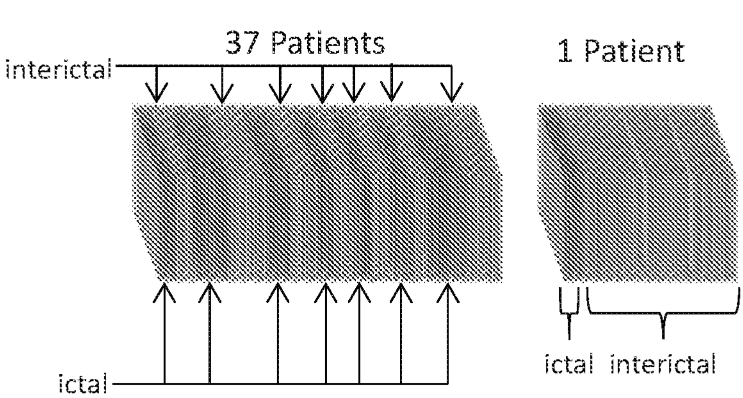

In some embodiments, to limit overfitting, the seizure recognition neural network 826 may be kept simple and shallow (see, Table 2), and training may be performed on matched data where both classes ("seizure" and "no seizure") appear equally often (FIG. 10A, FIG. 10B). However, other techniques for training may be employed. In some embodiments, the seizure recognition neural network 826 may be trained in a supervised fashion, on a set of training sequences (e.g., the matched data), using an optimization algorithm, such as, e.g., gradient descent, combined with backpropagation through time to compute the gradients needed during the optimization process, in order to change each weight of the LSTM network in proportion to the derivative of the error (at the output layer of the LSTM network) with respect to corresponding weight.

In some embodiments, based on the training, the seizure forecasting neural network 826 may ingest the encoded data and automatically determine a probability of a seizure occurrence captured in the video data 802 and the biometric sensor data 803. As described above, the probability may be a decimal number between 0 and 1. Thus, to produce a classification 804 for the epoch of sensor data, the seizure recognition neural network 826 may compare the seizure probability to a classification threshold. In some embodiments, classification threshold may include a value selected to balance the risks of false positives (an incorrect classification of a seizure occurrence) and false negatives (an incorrect classification no seizure occurrence). In some scenarios, an incorrect determination of "no seizure" may result in patient harm due to lack of care, whereas an incorrect determination of "seizure" may simply result in an unnecessary patient interaction. Thus, due to increased risks of patient harm for false negatives, the classification threshold may be selected to bias towards false positives to limit false negatives, such as a minimum probability of, e.g., 0.6. For example, the classification threshold may include a value of about, e.g., 0.4, 0.5, 0.6, 0.7, 0.8, 0.9 or other threshold. As a result, the seizure recognition engine 720 may produce a classification 804 from the video data 802 in real-time whether a patient is experiencing a seizure.

Figure 9:
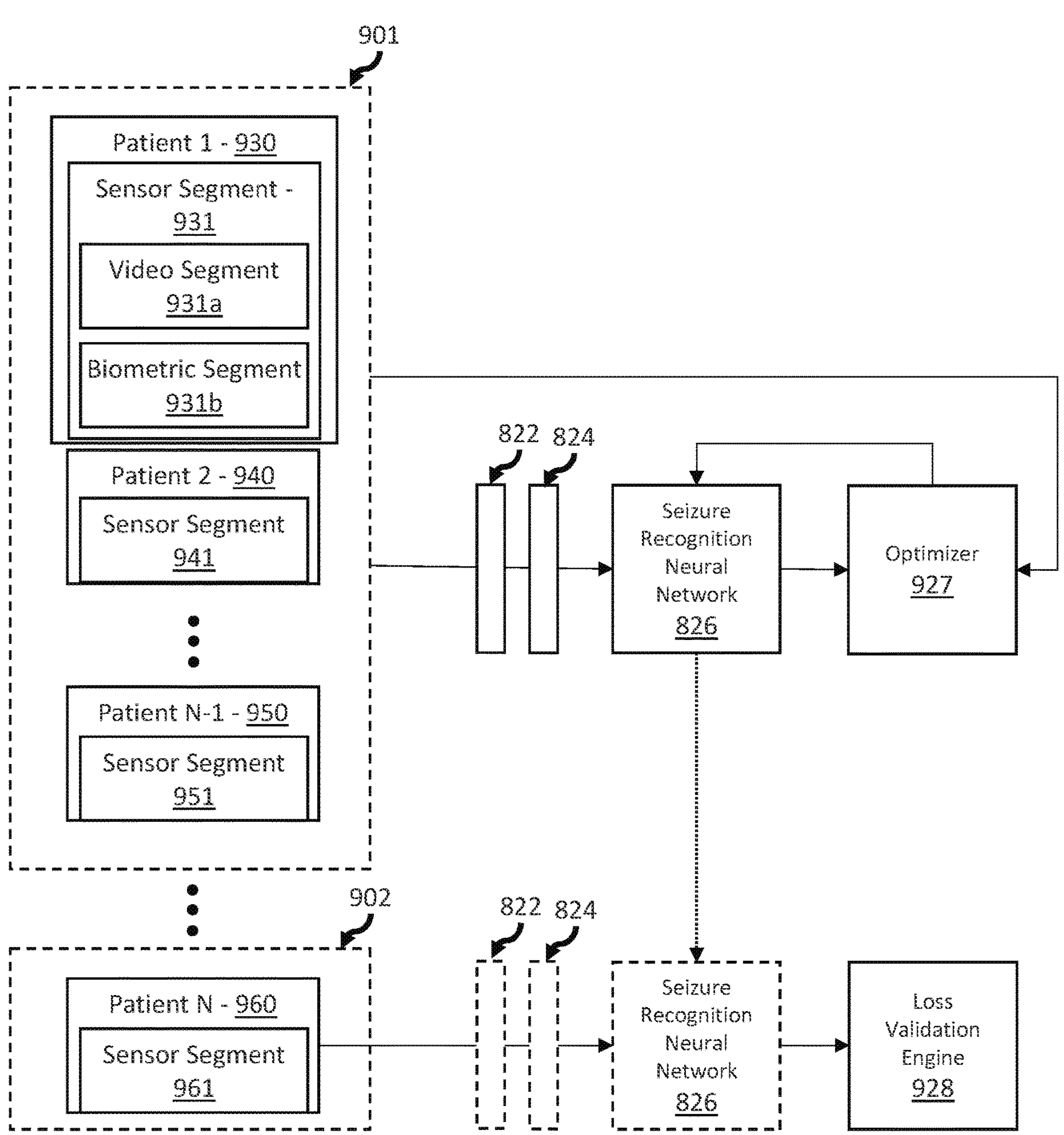
FIG. 9 illustrates an example of a schematic outline of a seizure detection model employed by a system for sensor-based detection of seizures and the training and testing thereof in accordance with one or more embodiments of the present invention.

FIG. 9 illustrates a block diagram of another exemplary computer-based system and platform including a seizure recognition engine including seizure forecasting neural network training and validation for seizure monitoring and seizure detection in accordance with one or more embodiments of the present disclosure.

Preparation of Training and Test Data

In some embodiments, segments of sensor data including a video segment of the video data and biometric sensor segment of the biometric sensor data for training may include recorded videos from epilepsy patients in the EMU. The sensor data for each segment for each patient corresponded with either normal, non-seizure situations, or during the course of a seizure of one or more particular types. In some embodiments, for training of the seizure recognition neural network 826 a subset of the patients include patient 1 930, patient 2 940 through patient N−1 950, with a testing dataset including a subset of the patients including patient N 960. In some embodiments, the training dataset 901 may include, e.g., 70 percent, 75 percent, 80 percent, 85 percent, 90 percent, percent, or other suitable proportion of the patients for training the seizure recognition neural network 826. In some embodiments, the remaining patients not in the training dataset 901 may be used as the testing dataset 902 to evaluate the performance of the seizure recognition neural network 826 upon training with the training dataset.

In some embodiments the data from each patient 930, 940, . . . , 950, 960 may include patient specific clinical data as input to further refine the seizure recognition neural network 826 to be a patient-specific model. For example, additional patient-specific clinical data may include, e.g., age, sex, age of seizure onset, etiology, seizure type, and semiology, seizure localization, seizure frequency, and medical comorbidities; there are also triggers of seizures, most prominently light stimulation, sleep deprivation, alcohol intake/withdrawal (seizures are most prominent when the alcohol level drops), hyperventilation, or ambient factors or any combination thereof.

In some embodiments, using the patient training dataset 901, the seizure recognition neural network 826 may be trained by an optimizer 927 to detect the sensor segment 931 through 951 during which the patient (930, 940, . . . , 950) experienced a seizure. To validate the training, a loss validation engine 928 may be employed with leave-one-out cross-validation, where matched data from all patients (930, 940, . . . , 950) but one are used for training, with the testing done on all of the sensor segments 961 from the remaining out-of-sample patient, patient N 960.

In some embodiments, for preparation of the training datasets 901, all sensor data are separated into consecutive 5-second sensor segments 931, 941, . . . , 951 and 961. In some embodiments, each sensor segment 931, 941, . . . , 951 includes a 5-second video segment 931*a* and 5-second biometric sensor segment 931*b*. All ictal 5-second segments are including for a patient for training and matched with an equal number of randomly chosen interictal 5-second sensor segments from the same patient. This matching may mitigate the imbalanced data during training where interictal data often outnumbers ictal data. Next, the matched data from 97 patients of the training dataset 901 may be used for training while testing is performed on the sensor segment 961 from the remaining patient, patient N 960, including the full sensor segment 961 of both ictal and interictal periods.

Neural Networks and Training

In some embodiments, the sensor segments 931, 941, . . . , 951 and 961 are downsampled by a signal processor 822. In some embodiments, the video segment 931*a* may be downsampled, e.g., from the original 30 Hz to 10 Hz, turned into grey-scale and resized to 224 by 224 pixel resolution, while each set of biometric sensor measurements in the biometric sensor segment 931*b* may be downsampled and/or analyzed for motion recognition. For encoding of individual samples of the video segment 931*a* and the biometric sensor segment 931*b*, a pretrained MobileNet excluding the top layers is employed as an encoder 824. In some embodiments, the seizure recognition neural network 826 may include long short-term memory networks (LSTMs) to encode the temporal sequence of these outputs, as LSTMs are specifically designed for learning underlying representations in timeseries data. To limit LSTMs from overfitting, architectures are kept simple and shallow (Table 2), and training is performed on matched data where both classes appear equally often (FIG. 10A, FIG. 10B).

Performance Metrics

In some embodiments, seizure occurrence detection performance may be assessed with sensitivity, specificity and time in warning. Sensitivity is defined as the fraction of seizures correctly detected, e.g., during which at least one 5-second epoch is classified as ictal. Specificity is defined as the fractions of true negative 5-second epochs during interictal data. Because of its more straight forward clinical interpretability, time in warning is also reported, which is defined as the complement of specificity (e.g., 1-specificity).

In some embodiments, the training dataset 901 and testing dataset 902 may include a suitable sample size of patient data, such as, e.g., 77 GTC seizures from 38 patients (e.g., age 13.59±4.66, 19 females). For each patient, interictal sensor segments (15.03±3.67 mm) are also included, during which patients are either sleeping or engaged in some activity. In an embodiments, a leave-one-out cross-validation approach is employed where patched ictal/interictal sensor segments 931, 941, . . . , 951 from 37 patients are used for training, and testing is done on the full sensor data segment 961 of the one remaining out-of-sample patient, patient N 960 (FIG. 10A, FIG. 10B). Seizure detection performance may be evaluated using sensitivity and specificity.

Figure 11:
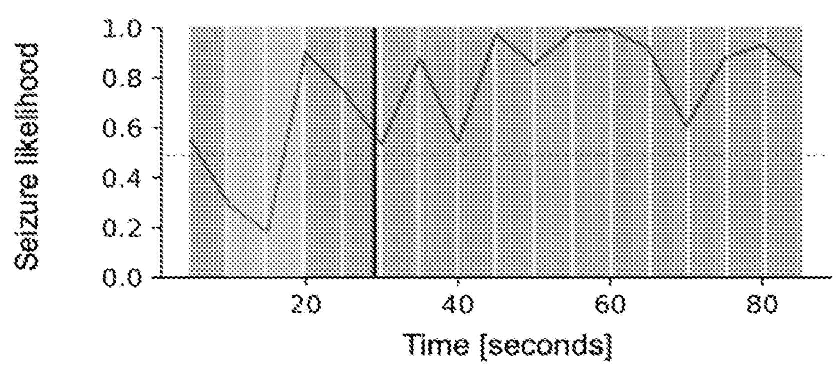
FIG. 11A and FIG. 11B depicts an example of a predicted seizure likelihood over the course of each seizure in accordance with one or more embodiments of the present invention.
Figure 11:
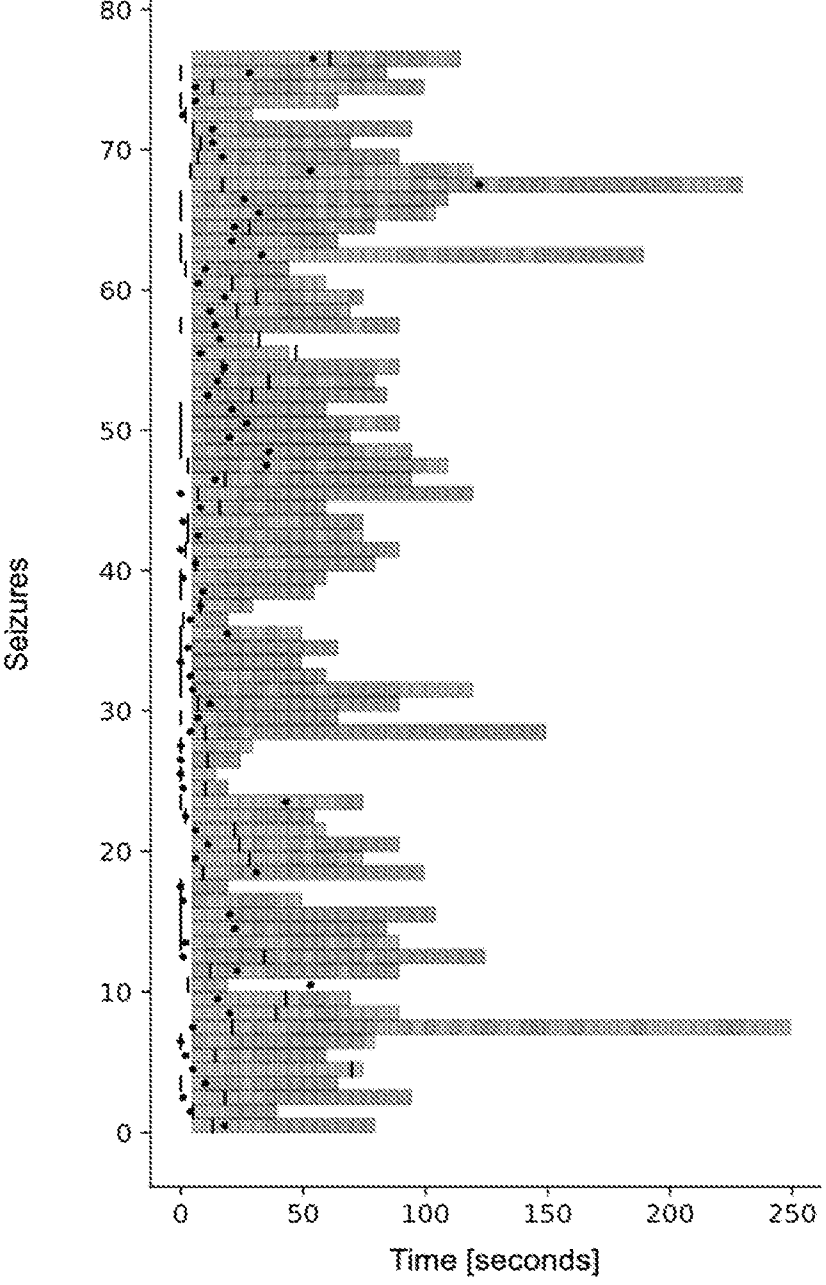

FIG. 11 shows the performance for the video segments of all 38 patients. In an embodiment, five of the 77 seizures were not detected. Across patients a mean sensitivity of 95.18±2.84% and a mean specificity of 81.61±4.46% are reported. The average latency by which a seizure is detected by an embodiment of the seizure recognition neural network 826 after the beginning of the tonic phase is 7.99±2.23 seconds. In some embodiments, adding the biometric sensor segments may improve both specificity and sensitivity of the model using transfer learning with the seizure recognition neural network 826 pretrained using only the video segments.

In a hospital setting, there are often caretakers and family members approaching the bed and the patient, which may impact the performance of a detection algorithm or potentially confine what the algorithm uses in order to detect a seizure. To determine whether embodiments of the present method would also detect seizures in the absence of any other persons in the video and biometric sensor data, the times when one or more persons apart from the patient appeared in the video and/or biometric sensor data for the first time may be labeled. FIG. 11 shows the time course of seizure likelihood for all patients along with an indication of when other persons appear in the video (black vertical lines) and the biometric sensor data. As is evident from this figure, an embodiment of the seizure recognition engine 720 correctly detected the seizure in more than 10% (8/77 seizures). Thus, a detection mechanism that solely detects a seizure based on whether other persons are visible can be ruled out.

FIGS. 10A and 10B depicts an example of an outline of data processing for automated video seizure detection, in accordance with one or more embodiments of the present invention. FIG. 10A depicts consecutive ictal sensor segments of 5 seconds duration (red) were matched with the same number of interictal sensor segments (green) for each patient, in accordance with one or more embodiments of the present invention. FIG. 10B depicts a leave-one-out cross-validation approach that trained on matched data from all but one patient and evaluated on the full data from the remaining patient was implemented to assess performance, in accordance with one or more embodiments of the present invention. An illustrative network architecture including a learning rate set to 0.001, batch size to 16, Adam optimizer, in accordance with one or more embodiments of the present invention for automated sensor-based seizure detection is presented below in Table 2:

TABLE 2

Automated Sensor-Based Seizure Detection Neural Network Architecture

| Layer Number | Layer Type | Filter/ Kernel Size or Nodes | Layer Parameters |
|---|---|---|---|
| 1 | MobileNet | N/A | Weights-imagenet, include_top = False |
| 2 | Flatten | N/A | N/A |
| 3 | Dropout | N/A | Dropout rate = 0.5 |
| 4 | LSTM | 100 | N/A |
| 6 | Dense | 1 | activation = sigmoid |

FIGS. 11A and 11B depict an example of a predicted seizure likelihood over the course of each seizure in accordance with one or more embodiments of the present invention. FIG. 11A depicts predicted seizure likelihood for one seizure, where likelihood is assessed every 5 seconds; if likelihood is smaller than 0.5 no seizure is detected (light gray), otherwise a seizure is detected during this 5-second epoch (dark gray), in accordance with one or more embodiments of the present invention. FIG. 11B depicts the likelihood time course for all seizures, where black vertical lines indicate the first time another person aside from the patient is visible in the video and black round markers indicate the onset of the tonic phase, in accordance with one or more embodiments of the present invention.

Figure 12:
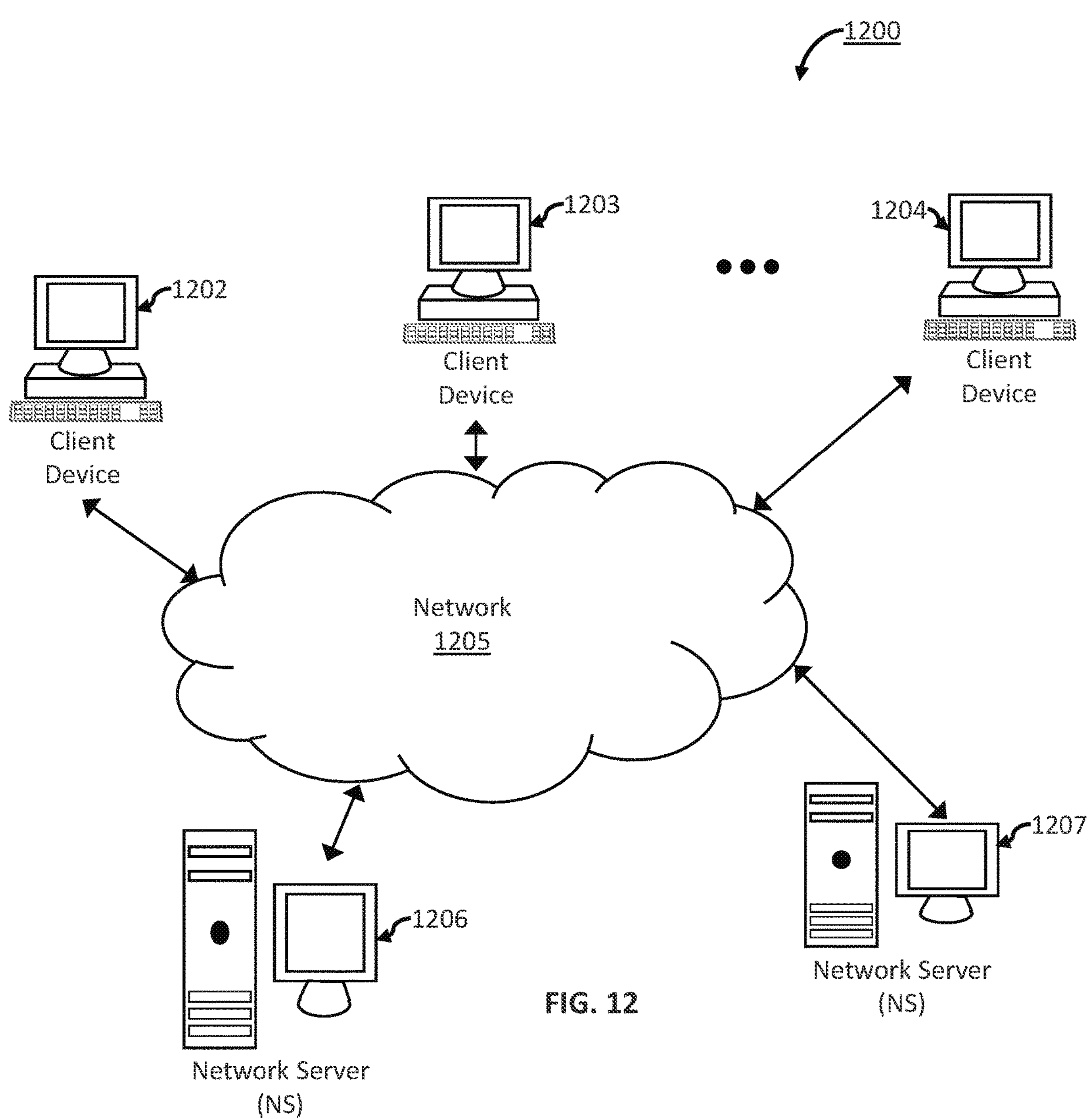
FIG. 12, FIG. 13, FIG. 14 and FIG. 15 depict examples of systems for implementing video-based detection of seizures in accordance with one or more embodiments of the present invention.

FIG. 12 depicts a block diagram of an exemplary computer-based system and platform 1200 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the illustrative computing devices and the illustrative computing components of the exemplary computer-based system and platform 1200 may be configured to manage a large number of members and concurrent transactions, as detailed herein. In some embodiments, the exemplary computer-based system and platform 1200 may be based on a scalable computer and network architecture that incorporates varies strategies for assessing the data, caching, searching, and/or database connection pooling. An example of the scalable architecture is an architecture that is capable of operating multiple servers.

In some embodiments, referring to FIG. 12, members 1202-1204 (e.g., clients) of the exemplary computer-based system and platform 1200 may include virtually any computing device capable of receiving and sending a message over a network (e.g., cloud network), such as network 1205, to and from another computing device, such as servers 1206 and 1207, each other, and the like. In some embodiments, the member devices 1202-1204 may be personal computers, multiprocessor systems, microprocessor-based or programmable consumer electronics, network PCs, and the like. In some embodiments, one or more member devices within member devices 1202-1204 may include computing devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile computing device, and the like. In some embodiments, one or more member devices within member devices 1202-1204 may be devices that are capable of connecting using a wired or wireless communication medium such as a PDA, POCKET PC, wearable computer, a laptop, tablet, desktop computer, a netbook, a video game device, a pager, a smart phone, an ultra-mobile personal computer (UMPC), and/or any other device that is equipped to communicate over a wired and/or wireless communication medium (e.g., NFC, RFID, NBIOT, 3G, 4G, 5G, GSM, GPRS, WiFi, WiMax, CDMA, satellite, ZigBee, etc.). In some embodiments, one or more member devices within member devices 1202-1204 may include may run one or more applications, such as Internet browsers, mobile applications, voice calls, video games, videoconferencing, and email, among others. In some embodiments, one or more member devices within member devices 1202-1204 may be configured to receive and to send web pages, and the like. In some embodiments, an exemplary specifically programmed browser application of the present disclosure may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, a member device within member devices 1202-1204 may be specifically programmed by either Java, .Net, QT, C, C++ and/or other suitable programming language. In some embodiments, one or more member devices within member devices 1202-1204 may be specifically programmed include or execute an application to perform a variety of possible tasks, such as, without limitation, messaging functionality, browsing, searching, playing, streaming or displaying various forms of content, including locally stored or uploaded messages, images and/or video, and/or games.

In some embodiments, the exemplary network 1205 may provide network access, data transport and/or other services to any computing device coupled to it. In some embodiments, the exemplary network 1205 may include and implement at least one specialized network architecture that may be based at least in part on one or more standards set by, for example, without limitation, Global System for Mobile communication (GSM) Association, the Internet Engineering Task Force (IETF), and the Worldwide Interoperability for Microwave Access (WiMAX) forum. In some embodiments, the exemplary network 1205 may implement one or more of a GSM architecture, a General Packet Radio Service (GPRS) architecture, a Universal Mobile Telecommunications System (UMTS) architecture, and an evolution of UMTS referred to as Long Term Evolution (LTE). In some embodiments, the exemplary network 1205 may include and implement, as an alternative or in conjunction with one or more of the above, a WiMAX architecture defined by the WiMAX forum. In some embodiments and, optionally, in combination of any embodiment described above or below, the exemplary network 1205 may also include, for instance, at least one of a local area network (LAN), a wide area network (WAN), the Internet, a virtual LAN (VLAN), an enterprise LAN, a layer 3 virtual private network (VPN), an enterprise IP network, or any combination thereof. In some embodiments and, optionally, in combination of any embodiment described above or below, at least one computer network communication over the exemplary network 1205 may be transmitted based at least in part on one of more communication modes such as but not limited to: NFC, RFID, Narrow Band Internet of Things (NBIOT), ZigBee, 3G, 4G, 5G, GSM, GPRS, WiFi, WiMax, CDMA, satellite and any combination thereof. In some embodiments, the exemplary network 1205 may also include mass storage, such as network attached storage (NAS), a storage area network (SAN), a content delivery network (CDN) or other forms of computer or machine readable media.

In some embodiments, the exemplary server 1206 or the exemplary server 1207 may be a web server (or a series of servers) running a network operating system, examples of which may include but are not limited to Microsoft Windows Server, Novell NetWare, or Linux. In some embodiments, the exemplary server 1206 or the exemplary server 1207 may be used for and/or provide cloud and/or network computing. Although not shown in FIG. 12, in some embodiments, the exemplary server 1206 or the exemplary server 1207 may have connections to external systems like email, SMS messaging, text messaging, ad content providers, etc. Any of the features of the exemplary server 1206 may be also implemented in the exemplary server 1207 and vice versa.

In some embodiments, one or more of the exemplary servers 1206 and 1207 may be specifically programmed to perform, in non-limiting example, as authentication servers, search servers, email servers, social networking services servers, SMS servers, IM servers, MMS servers, exchange servers, photo-sharing services servers, advertisement providing servers, financial/banking-related services servers, travel services servers, or any similarly suitable service-base servers for users of the member computing devices 1201-1204.

In some embodiments and, optionally, in combination of any embodiment described above or below, for example, one or more exemplary computing member devices 1202-1204, the exemplary server 1206, and/or the exemplary server 1207 may include a specifically programmed software module that may be configured to send, process, and receive information using a scripting language, a remote procedure call, an email, a tweet, Short Message Service (SMS), Multimedia Message Service (MMS), instant messaging (IM), internet relay chat (IRC), mIRC, Jabber, an application programming interface, Simple Object Access Protocol (SOAP) methods, Common Object Request Broker Architecture (CORBA), HTTP (Hypertext Transfer Protocol), REST (Representational State Transfer), or any combination thereof.

Figure 13:
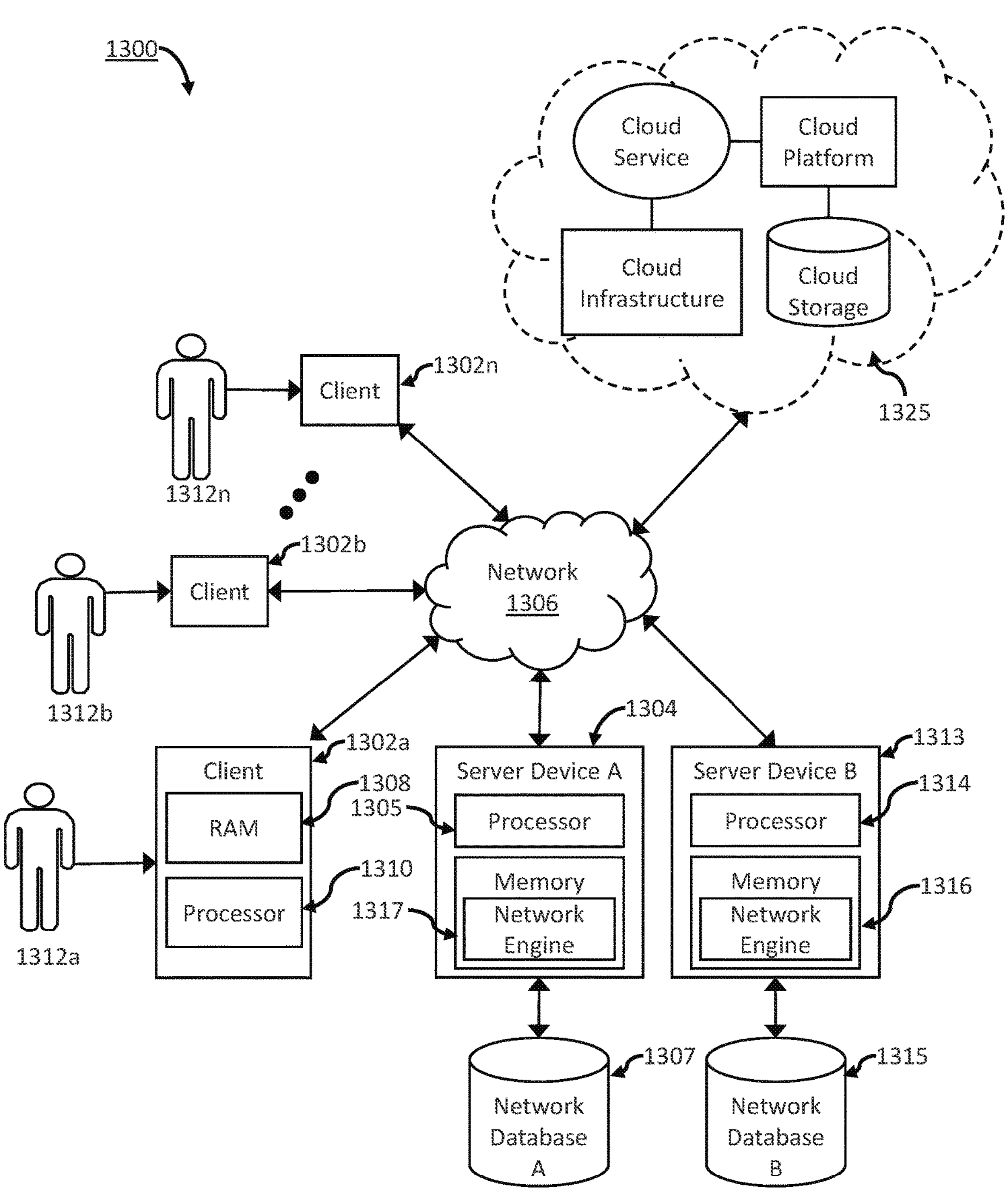

FIG. 13 depicts a block diagram of another exemplary computer-based system and platform 1300 in accordance with one or more embodiments of the present disclosure. However, not all of these components may be required to practice one or more embodiments, and variations in the arrangement and type of the components may be made without departing from the spirit or scope of various embodiments of the present disclosure. In some embodiments, the member computing devices 1302*a*, 1302*b* thru 1302*n* shown each at least includes a computer-readable medium, such as a random-access memory (RAM) 1308 coupled to a processor 1310 or FLASH memory. In some embodiments, the processor 1310 may execute computer-executable program instructions stored in memory 1308. In some embodiments, the processor 1310 may include a microprocessor, an ASIC, and/or a state machine. In some embodiments, the processor 1310 may include, or may be in communication with, media, for example computer-readable media, which stores instructions that, when executed by the processor 1310, may cause the processor 1310 to perform one or more steps described herein. In some embodiments, examples of computer-readable media may include, but are not limited to, an electronic, optical, magnetic, or other storage or transmission device capable of providing a processor, such as the processor 1310 of client 1302*a*, with computer-readable instructions. In some embodiments, other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. In some embodiments, the instructions may comprise code from any computer-programming language, including, for example, C, C++, Visual Basic, Java, Python, Perl, JavaScript, and etc.

In some embodiments, member computing devices 1302*a* through 1302*n* may also comprise a number of external or internal devices such as a mouse, a CD-ROM, DVD, a physical or virtual keyboard, a display, or other input or output devices. In some embodiments, examples of member computing devices 1302*a* through 1302*n* (e.g., clients) may be any type of processor-based platforms that are connected to a network 1306 such as, without limitation, personal computers, digital assistants, personal digital assistants, smart phones, pagers, digital tablets, laptop computers, Internet appliances, and other processor-based devices. In some embodiments, member computing devices 1302*a* through 1302*n* may be specifically programmed with one or more application programs in accordance with one or more principles/methodologies detailed herein. In some embodiments, member computing devices 1302*a* through 1302*n* may operate on any operating system capable of supporting a browser or browser-enabled application, such as Microsoft™, Windows™, and/or Linux. In some embodiments, member computing devices 1302*a* through 1302*n* shown may include, for example, personal computers executing a browser application program such as Microsoft Corporation's Internet Explorer™, Apple Computer, Inc.'s Safari™, Mozilla Firefox, and/or Opera. In some embodiments, through the member computing client devices 1302*a* through 1302*n*, users, 1312*a* through 1302*n*, may communicate over the exemplary network 1306 with each other and/or with other systems and/or devices coupled to the network 1306. As shown in FIG. 13, exemplary server devices 1304 and 1313 may be also coupled to the network 1306. In some embodiments, one or more member computing devices 1302*a* through 1302*n* may be mobile clients.

In some embodiments, at least one database of exemplary databases 1307 and 1315 may be any type of database, including a database managed by a database management system (DBMS). In some embodiments, an exemplary DBMS-managed database may be specifically programmed as an engine that controls organization, storage, management, and/or retrieval of data in the respective database. In some embodiments, the exemplary DBMS-managed database may be specifically programmed to provide the ability to query, backup and replicate, enforce rules, provide security, compute, perform change and access logging, and/or automate optimization. In some embodiments, the exemplary DBMS-managed database may be chosen from Oracle database, IBM DB2, Adaptive Server Enterprise, FileMaker, Microsoft Access, Microsoft SQL Server, MySQL, PostgreSQL, and a NoSQL implementation. In some embodiments, the exemplary DBMS-managed database may be specifically programmed to define each respective schema of each database in the exemplary DBMS, according to a particular database model of the present disclosure which may include a hierarchical model, network model, relational model, object model, or some other suitable organization that may result in one or more applicable data structures that may include fields, records, files, and/or objects. In some embodiments, the exemplary DBMS-managed database may be specifically programmed to include metadata about the data that is stored.

Figure 14:
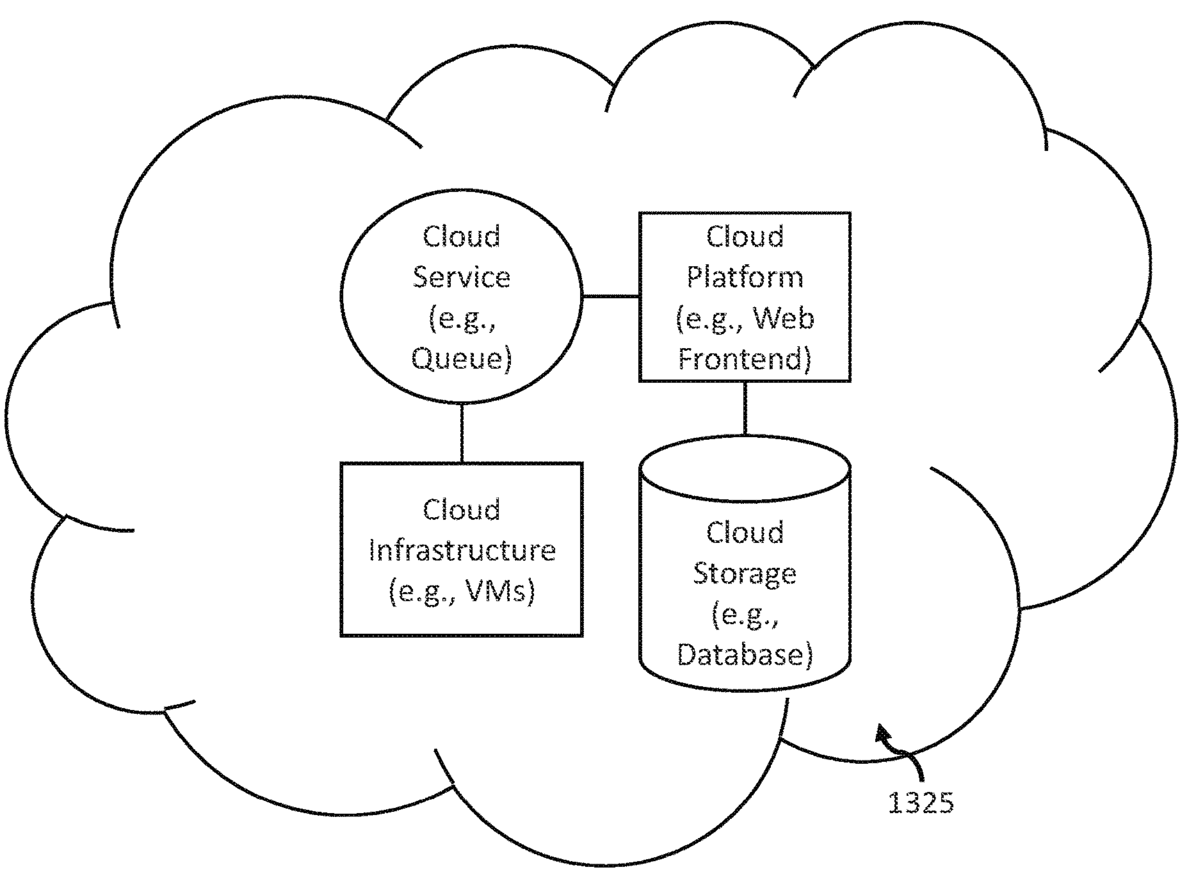
Figure 15:
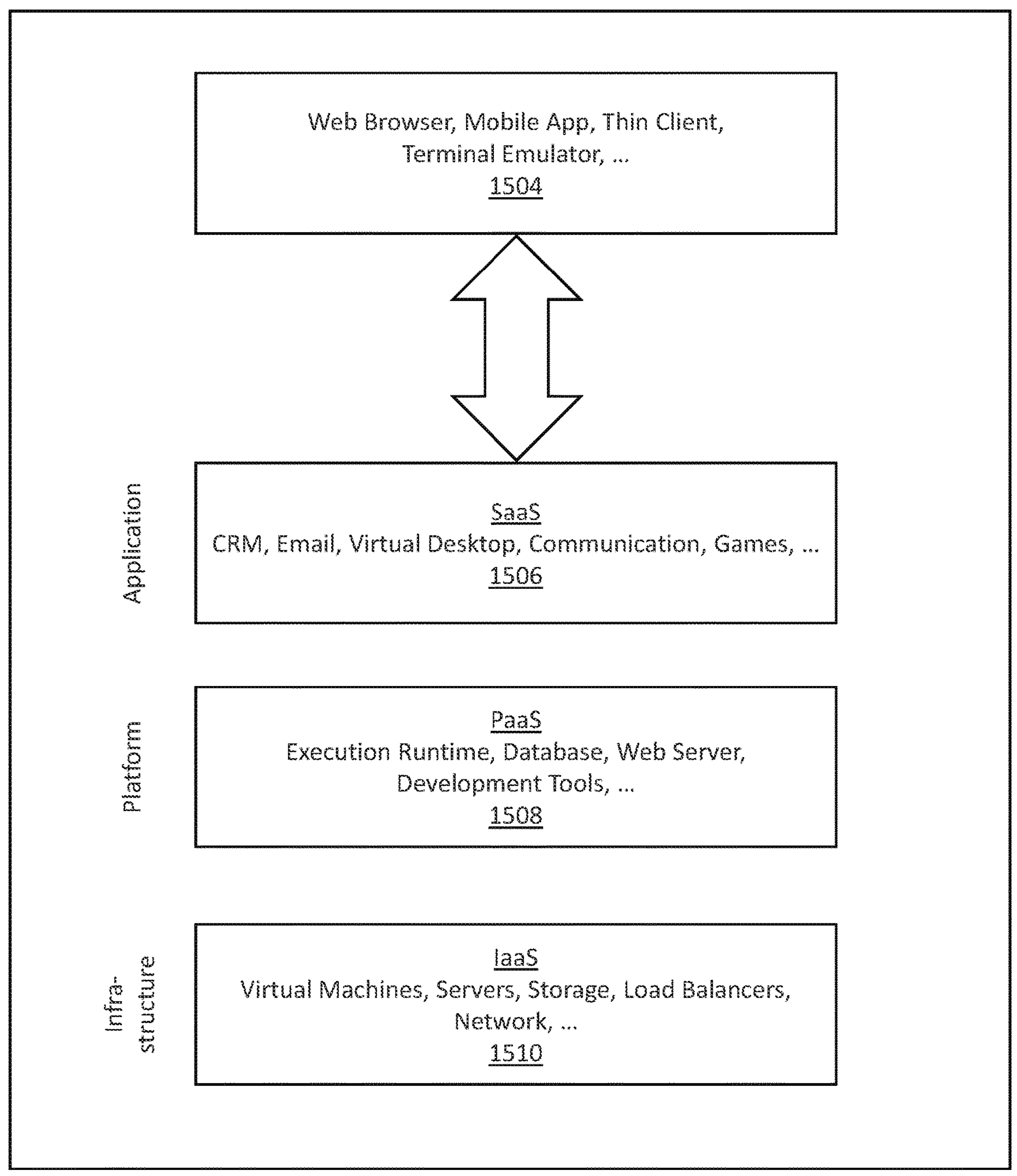

In some embodiments, the exemplary inventive computer-based systems/platforms, the exemplary inventive computer-based devices, and/or the exemplary inventive computer-based components of the present disclosure may be specifically configured to operate in a cloud computing/architecture 1325 such as, but not limiting to: infrastructure a service (IaaS) 1510, platform as a service (PaaS) 1508, and/or software as a service (SaaS) 1506 using a web browser, mobile app, thin client, terminal emulator or other endpoint 1504. FIGS. 14 and 15 illustrate schematics of exemplary implementations of the cloud computing/architecture(s) in which the exemplary inventive computer-based systems/platforms, the exemplary inventive computer-based devices, and/or the exemplary inventive computer-based components of the present disclosure may be specifically configured to operate.

The aforementioned examples are, of course, illustrative and not restrictive.

At least some aspects of the present disclosure will now be described with reference to the following numbered clauses.

1. A method including:
   receiving, by at least one processor, real-time video data including a continuous video feed of a patient location;
   extracting, by the at least one processor, an epoch of video data including a video segment from the continuous video feed from a patient monitoring period preceding a current time;
   generating, by the at least one processor, time-series data representative of the epoch of video data;
   utilizing, by the at least one processor, seizure recognition machine learning model to determine a seizure classification of the video segment including either a seizure video segment classification or no-seizure video segment classification based on the time-series data and learned model parameters; and
   causing to produce, by the at least one processor, a seizure indication at a computing device associated with a caregiver for each video segment identified as a seizure video segment to alert the caregiver of a seizure.
2. The method as recited in clause 1, further including encoding, by the at least one processor, the epoch of video data into the time-series data using a pre-trained encoding model.
3. The method as recited in clause 2, where the pre-trained encoding model includes MobileNet.
4. The method as recited in clause 1, further including downsampling, by the at least one processor, the video segment by downsample one of:

i) frame rate,
ii) color data,
iii) resolution, or
iv) combinations thereof.

5. The method as recited in clause 1, where the seizure recognition machine learning model includes a recurrent neural network.

6. The method as recited in clause 1, where the seizure recognition machine learning model includes a long short-term memory network.

7. The method as recited in clause 1, further including:
determining, by the at least one processor, a seizure probability value using the seizure recognition machine learning model based on the time-series data; and
determining, by the at least one processor, the seizure classification of the video segment based on a comparison of the seizure probability value to a classification threshold.

8. The method as recited in clause 7, where the seizure classification includes the no seizure video segment classification where the seizure probably value is less than the classification threshold.

9. The method as recited in clause 1, where the patient monitoring period includes 5 seconds associated with the epoch of video data including 5 seconds of video data.

10. The method as recited in clause 1, further including utilizing, by the at least one processor, the seizure recognition machine learning model for each subsequent epoch of video data received in the continuous video feed.

11. A system including:
at least one processor configured to receive instructions stored in a non-transitory memory that cause the at least one processor to perform steps to:
receive real-time video data including a continuous video feed of a patient location;
extract an epoch of video data including a video segment from the continuous video feed from a patient monitoring period preceding a current time;
generate time-series data representative of the epoch of video data;
utilize seizure recognition machine learning model to determine a seizure classification of the video segment including either a seizure video segment classification or no-seizure video segment classification based on the time-series data and learned model parameters; and
cause to produce a seizure indication at a computing device associated with a caregiver for each video segment identified as a seizure video segment to alert the caregiver of a seizure.

12. The system as recited in clause 11, where the at least one processor is further configured to receive instructions causing the at least one processor to perform steps to encode the epoch of video data into the time-series data using a pre-trained encoding model.

13. The system as recited in clause 12, where the pre-trained encoding model includes MobileNet.

14. The system as recited in clause 11, where the at least one processor is further configured to receive instructions causing the at least one processor to perform steps to downsample the video segment by downsample one of:
i) frame rate,
ii) color data,
iii) resolution, or
iv) combinations thereof.

15. The system as recited in clause 11, where the seizure recognition machine learning model includes a recurrent neural network.

16. The system as recited in clause 11, where the seizure recognition machine learning model includes a long short-term memory network.

17. The system as recited in clause 11, where the at least one processor is further configured to receive instructions causing the at least one processor to perform steps to:
determine a seizure probability value using the seizure recognition machine learning model based on the time-series data; and
determine the seizure classification of the video segment based on a comparison of the seizure probability value to a classification threshold.

18. The system as recited in clause 17, where the seizure classification includes the no seizure video segment classification where the seizure probably value is less than the classification threshold.

19. The system as recited in clause 11, where the patient monitoring period includes 5 seconds associated with the epoch of video data including 5 seconds of video data.

20. The method as recited in clause 11, where the at least one processor is further configured to receive instructions causing the at least one processor to perform steps to utilize the seizure recognition machine learning model for each subsequent epoch of video data received in the continuous video feed.

21. A method including:
receiving, by at least one processor, real-time video data including a continuous video feed of a patient location;
extracting, by the at least one processor, an epoch of video data including a video segment from the continuous video feed from a patient monitoring period preceding a current time;
receiving, by at least one processor, real-time biometric sensor data including a continuous feed of biometric measurements;
extracting, by the at least one processor, an epoch of biometric sensor data including a biometric measurement segment from the continuous feed of biometric measurements from the patient monitoring period preceding the current time;
generating, by the at least one processor, time-series data representative of the epoch of video data and the epoch of biometric sensor data;
utilizing, by the at least one processor, seizure recognition machine learning model to determine a seizure classification for the patient monitoring period based on the time-series data and learned model parameters; and
causing to produce, by the at least one processor, a seizure indication at a computing device associated with a caregiver for the patient monitoring period that indicates the seizure classification to alert the caregiver.

22. The method as recited in clause 21, further including encoding, by the at least one processor, the epoch of video data into the time-series data using a pre-trained encoding model.

23. The method as recited in clause 21, where the biometric sensor includes at least one of:
a surface electromyography (sEMG) sensor,
an electrodermal activity (EDA) sensor,
an electrocardiogram (EKG) sensor,
a photoplethysmography (PPG) sensor,
an accelerometer,
a mattress sensor,
a cerebral oxygen saturation sensor, a near-infrared spectroscopy (NIRS) sensor,
an implanted advisory system,
a skin temperature sensor,
a respiratory monitor,
a magnetometer, and
a gyroscope.

24. The method as recited in clause 21, further including downsampling, by the at least one processor, the video segment by downsample one of:
i) frame rate,
ii) color data,
iii) resolution, or
iv) combinations thereof.

25. The method as recited in clause 21, where the seizure recognition machine learning model includes a recurrent neural network.

26. The method as recited in clause 21, where the seizure recognition machine learning model includes a long short-term memory network.

27. The method as recited in clause 21, further including:
determining, by the at least one processor, a seizure probability value using the seizure recognition machine learning model based on the time-series data; and
determining, by the at least one processor, the seizure classification based on a comparison of the seizure probability value to a classification threshold.

28. The method as recited in clause 27, where the seizure classification includes a no seizure classification where the seizure probability value is less than the classification threshold.

29. The method as recited in clause 21, where the patient monitoring period includes 5 seconds associated with the epoch of video data and the epoch of biometric sensor data.

30. The method as recited in clause 21, further including utilizing, by the at least one processor, the seizure recognition machine learning model for each subsequent epoch of video data received in the continuous video feed.

31. A system including:
at least one processor configured to receive instructions stored in a non-transitory memory that cause the at least one processor to perform steps to:
receive real-time video data including a continuous video feed of a patient location;
extract an epoch of video data including a video segment from the continuous video feed from a patient monitoring period preceding a current time;
receive real-time biometric sensor data including a continuous feed of biometric measurements;
extract an epoch of biometric sensor data including a biometric measurement segment from the continuous feed of biometric measurements from the patient monitoring period preceding the current time;
generate time-series data representative of the epoch of video data and the epoch of biometric sensor data;
utilize seizure recognition machine learning model to determine a seizure classification for the patient monitoring period based on the time-series data and learned model parameters; and
cause to produce a seizure indication at a computing device associated with a caregiver for the patient monitoring period that indicates the seizure classification to alert the caregiver.

32. The system as recited in clause 31, where the at least one processor is further configured to receive instructions causing the at least one processor to perform steps to encode the epoch of video data into the time-series data using a pre-trained encoding model.

33. The system as recited in clause 31, where the biometric sensor includes at least one of:
a surface electromyography (sEMG) sensor,
an electrodermal activity (EDA) sensor,
an electrocardiogram (EKG) sensor,
a photoplethysmography (PPG) sensor,
an accelerometer,
a mattress sensor,
a cerebral oxygen saturation sensor,
a near-infrared spectroscopy (NIRS) sensor,
an implanted advisory system,
a skin temperature sensor,
a respiratory monitor,
a magnetometer, and
a gyroscope.

34. The system as recited in clause 31, where the at least one processor is further configured to receive instructions causing the at least one processor to perform steps to downsample the video segment by downsample one of:
i) frame rate,
ii) color data,
iii) resolution, or
iv) combinations thereof.

35. The system as recited in clause 31, where the seizure recognition machine learning model includes a recurrent neural network.

36. The system as recited in clause 31, where the seizure recognition machine learning model includes a long short-term memory network.

37. The system as recited in clause 31, where the at least one processor is further configured to receive instructions causing the at least one processor to perform steps to:
determine a seizure probability value using the seizure recognition machine learning model based on the time-series data; and
determine the seizure classification of the video segment based on a comparison of the seizure probability value to a classification threshold.

38. The system as recited in clause 37, where the seizure classification includes a no seizure classification where the seizure probability value is less than the classification threshold.

39. The system as recited in clause 31, where the patient monitoring period includes a time period of 5 seconds associated with the epoch of video data and the epoch of biometric sensor data.

40. The system as recited in clause 31, where the at least one processor is further configured to receive instructions causing the at least one processor to perform steps to utilize the seizure recognition machine learning model for each subsequent epoch of video data received in the continuous video feed.

While one or more embodiments of the present disclosure have been described, it is understood that these embodiments are illustrative only, and not restrictive, and that many modifications may become apparent to those of ordinary skill in the art, including that various embodiments of the inventive methodologies, the illustrative systems and platforms, and the illustrative devices described herein can be utilized in any combination with each other. Further still, the various steps may be carried out in any desired order (and any desired steps may be added and/or any desired steps may be eliminated).

What is claimed is:

1. A method comprising:

receiving, by at least one processor, real-time video data comprising a continuous video feed of a patient location;

extracting, by the at least one processor, an epoch of video data comprising a video segment from the continuous video feed from a patient monitoring period preceding a current time;

inputting, by the at least one processor, the video segment of the epoch of video data into an encoding neural network to convert the video segment into a sequence of video encodings representative of the epoch of video data, the sequence of video encodings forming time-series data representative of the epoch of video data;

inputting, by the at least one processor, each video encoding of the sequence of video encodings into a seizure recognition machine learning model configured to output a seizure classification of the video segment, comprising either a seizure video segment classification or no-seizure video segment classification, the seizure recognition machine learning model comprising at least one layer of long short term memory (LSTM) having learned model parameters; and causing to produce, in real time, by the at least one processor, a seizure indication at a computing device associated with a caregiver for each video segment identified as a seizure video segment to alert the caregiver of a seizure.

2. The method as recited in claim 1, further comprising encoding, by the at least one processor, the epoch of video data into the time-series data using the encoding neural network comprising a pre-trained encoding convolutional neural network having at least one top layer removed.

3. The method as recited in claim 2, wherein the pre-trained encoding model comprises MobileNet.

4. The method as recited in claim 1, further comprising downsampling, by the at least one processor, the video segment by downsample one of:

i) frame rate, ii) color data, iii) resolution, or iv) combinations thereof.

5. The method as recited in claim 1, wherein the seizure recognition machine learning model comprises a recurrent neural network.

6. The method as recited in claim 1, wherein the seizure recognition machine learning model comprises a long short-term memory network.

7. The method as recited in claim 1, further comprising:

determining, by the at least one processor, a seizure probability value using the seizure recognition machine learning model based on the time-series data; and determining, by the at least one processor, the seizure classification of the video segment based on a comparison of the seizure probability value to a classification threshold.

8. The method as recited in claim 7, wherein the seizure classification comprises the no seizure video segment classification where the seizure probably value is less than the classification threshold.

9. The method as recited in claim 1, wherein the patient monitoring period comprises 5 seconds associated with the epoch of video data comprising 5 seconds of video data.

10. The method as recited in claim 1, further comprising utilizing, by the at least one processor, the seizure recognition machine learning model for each subsequent epoch of video data received in the continuous video feed.

11. A system comprising:

at least one processor configured to receive instructions stored in a non-transitory memory that cause the at least one processor to perform steps to:

receive real-time video data comprising a continuous video feed of a patient location;

extract an epoch of video data comprising a video segment from the continuous video feed from a patient monitoring period preceding a current time;

input the video segment of the epoch of video data into an encoding neural network to convert the video segment into sequence of video encodings representative of the epoch of video data, the sequence of video encodings forming time-series data representative of the epoch of video data;

input each video encoding of the sequence of video encodings into a seizure recognition machine learning model configured to output a seizure classification of the video segment, comprising either a seizure video segment classification or no-seizure video segment classification, the seizure recognition machine learning model comprising at least one layer of long short term memory (LSTM) having learned model parameters; and cause to produce, in real time, a seizure indication at a computing device associated with a caregiver for each video segment identified as a seizure video segment to alert the caregiver of a seizure.

12. The system as recited in claim 11, wherein the at least one processor is further configured to receive instructions causing the at least one processor to perform steps to encode the epoch of video data into the time-series data using the encoding neural network comprising a pre-trained encoding convolutional neural network having at least one top layer removed.

13. The system as recited in claim 12, wherein the pre-trained encoding model comprises MobileNet.

14. The system as recited in claim 11, wherein the at least one processor is further configured to receive instructions causing the at least one processor to perform steps to downsample the video segment by downsample one of:

i) frame rate, ii) color data, iii) resolution, or iv) combinations thereof.

15. The system as recited in claim 11, wherein the seizure recognition machine learning model comprises a recurrent neural network.

16. The system as recited in claim 11, wherein the seizure recognition machine learning model comprises a long short-term memory network.

17. The system as recited in claim 11, wherein the at least one processor is further configured to receive instructions causing the at least one processor to perform steps to:

determine a seizure probability value using the seizure recognition machine learning model based on the time-series data; and determine the seizure classification of the video segment based on a comparison of the seizure probability value to a classification threshold.

18. The system as recited in claim 17, wherein the seizure classification comprises the no seizure video segment classification where the seizure probably value is less than the classification threshold.

19. The system as recited in claim 11, wherein the patient monitoring period comprises 5 seconds associated with the epoch of video data comprising 5 seconds of video data.

20. The system as recited in claim 11, wherein the at least one processor is further configured to receive instructions causing the at least one processor to perform steps to utilize the seizure recognition machine learning model for each subsequent epoch of video data received in the continuous video feed.

* * * * *